United States Patent
Kamal et al.

(10) Patent No.: US 8,461,150 B2
(45) Date of Patent: Jun. 11, 2013

(54) CHALCONE LINKED PYRROLO[2,1-C][1,4]BENZODIAZEPINE HYBRIDS AS POTENTIAL ANTICANCER AGENTS AND PROCESS FOR THE PREPARATION THEREOF

(75) Inventors: Ahmed Kamal, Andhra Pradesh (IN); Bandari Rajendra Prasad, Andhra Pradesh (IN); Adla Malla Reddy, Andhra Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 26 days.

(21) Appl. No.: 12/921,016

(22) PCT Filed: Oct. 31, 2008

(86) PCT No.: PCT/IN2008/000721
§ 371 (c)(1),
(2), (4) Date: Feb. 16, 2011

(87) PCT Pub. No.: WO2009/109986
PCT Pub. Date: Sep. 11, 2009

(65) Prior Publication Data
US 2011/0201600 A1     Aug. 18, 2011

(30) Foreign Application Priority Data
Mar. 5, 2008 (IN) .............................. 537/DEL/2008

(51) Int. Cl.
*C07D 487/04* (2006.01)
*A61K 31/5517* (2006.01)
*A61P 35/00* (2006.01)

(52) U.S. Cl.
USPC .......................................... 514/220; 540/496

(58) Field of Classification Search
USPC .......................................... 540/496; 514/220
See application file for complete search history.

(56) References Cited

FOREIGN PATENT DOCUMENTS
WO     2008/020455 A2     2/2008

OTHER PUBLICATIONS

Ahmed Kamal, et al; "Synthesis and biological activity of fluoroquinolone-pyrrolo[2, 1-c] [1,4]benzodiazepine conjugates",Bioorganic & Medicinal Chemistry, Elsevier Science Ltd, GB, vol. 13, No. 6, Mar. 15, 2005, pp. 2021-2029, XP004759003, ISSN: 0968-0896, The Whole Document.

Ahmed Kamal, et al; "Synthesis of C8-linked pyrrolo[2, 1-c][1,4]benzodiazepine-benzimidazole conjugates with remarkable DNA-binding affinity", Bioorganic & Medicinal Chemistry, Elsevier Science Ltd, GB, vol. 14, 2004, pp. 4791-4794, XP002517904, The Whole Document.
International Search Report: PCT/IN2008/000721, (2008).

*Primary Examiner* — Bruck Kifle
(74) *Attorney, Agent, or Firm* — Ladas & Parry LLP

(57) ABSTRACT

The present invention relates to chalcone linked pyrrolo[2,1-c][1,4]benzodiazepine hybrids and a process for the preparation there of. More particularly it relates to 7-Methoxy-8-{n[4-1-(2 or 4-substituted phenyl)-3-(4-hydroxy-3-methoxyphenyl)-2-propen-1-one]alkyl}-oxy}-(11aS)-1,2,3,11a-5H-pyrrolo[2,1-c][1,4]benzodiazepin-5-one and 7-Methoxy-8-{n-[-3-(4-hydroxy-3-methoxyphenyl)-1-(2,4-alkyl-3-quinolyl)-2-propen-1-one]alkyl}-oxy-(11aS)-1,2,3,11a-5H-pyrrolo[2,1-c][1,4]benzodiazepin-5-one with aliphatic chain length variations useful as anticancer (antitumor) agent. The general structural formula of these chalcone linked pyrrolo[2,1-c][1,4]benzodiazepines hybrids is given below. wherein $R^1$=OH, methyl, ethyl or phenyl; $R^2$=H, OH or F; R=H or methyl; x=c or N; n=1-4.

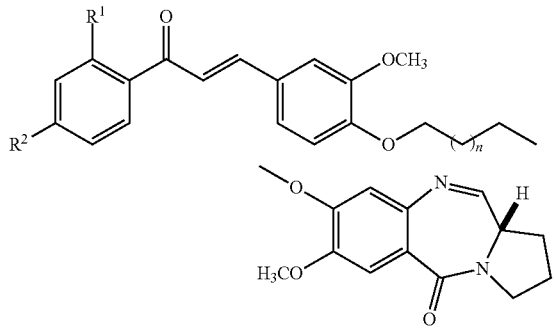

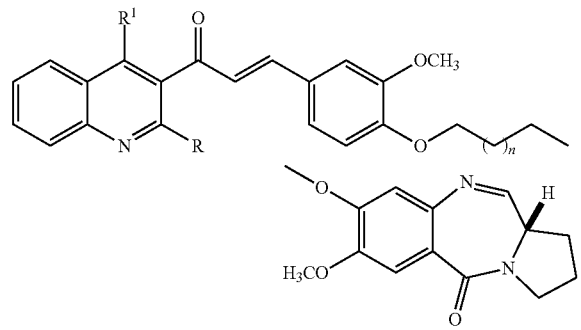

10 Claims, No Drawings

CHALCONE LINKED PYRROLO[2,1-C][1,4]BENZODIAZEPINE HYBRIDS AS POTENTIAL ANTICANCER AGENTS AND PROCESS FOR THE PREPARATION THEREOF

FIELD OF THE INVENTION

The present invention relates to chalcone linked pyrrolo[2,1-c][1,4]benzodiazepine hybrids and a process for the preparation there of. More particularly it relates to 7-Methoxy-8-{n-[4-1-(2 or 4-substituted phenyl)-3-(4-hydroxy-3-methoxyphenyl)-2-propen-1-one]alkyl}-oxy}-(11aS)-1,2,3,11a-5H-pyrrolo[2,1-c][1,4]benzodiazepin-5-one and 7-Methoxy-8-{n-[-3-(4-hydroxy-3-methoxyphenyl)-1-(2,4-alkyl-3-quinolyl)-2-propen-1-one]alkyl}-oxy-(11aS)-1,2,3,11a-5H-pyrrolo[2,1-c][1,4]benzodiazepin-5-one with aliphatic chain length variations useful as anticancer (antitumour) agent. The general structural formula of these chalcone linked pyrrolo[2,1-c][1,4]benzodiazepines hybrids is given below.

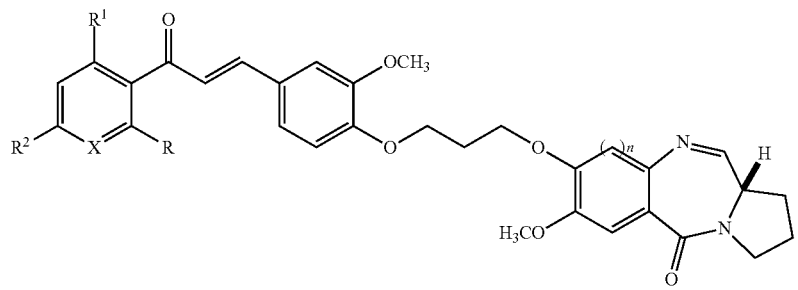

wherein $R^1$=OH, methyl, ethyl or phenyl; $R^2$=H, OH or F; R=H or methyl; x=c or N; n=1-4

Formula 6a-i and 10a-I

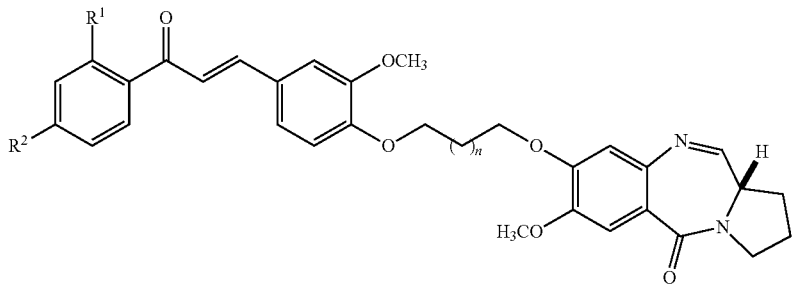

6a-i $R^1$ = OH
$R^2$ = OH, F
n = 1, 2, 3

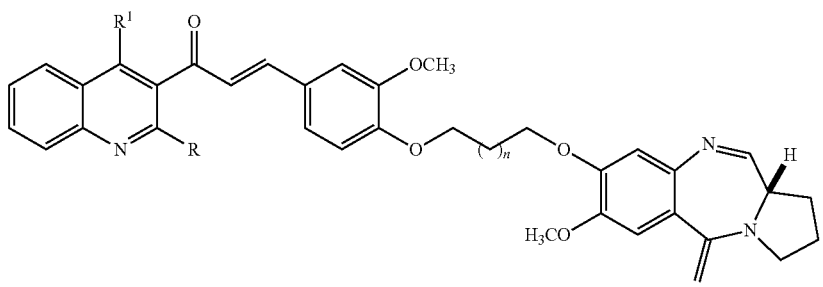

10a-I $R^1$ = methyl, ethyl, phenyl
R = methyl
n = 1, 2, 3, 4
n = 1, 2, 3, 4

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; Unezawa, H. *J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochemistry*, 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141).

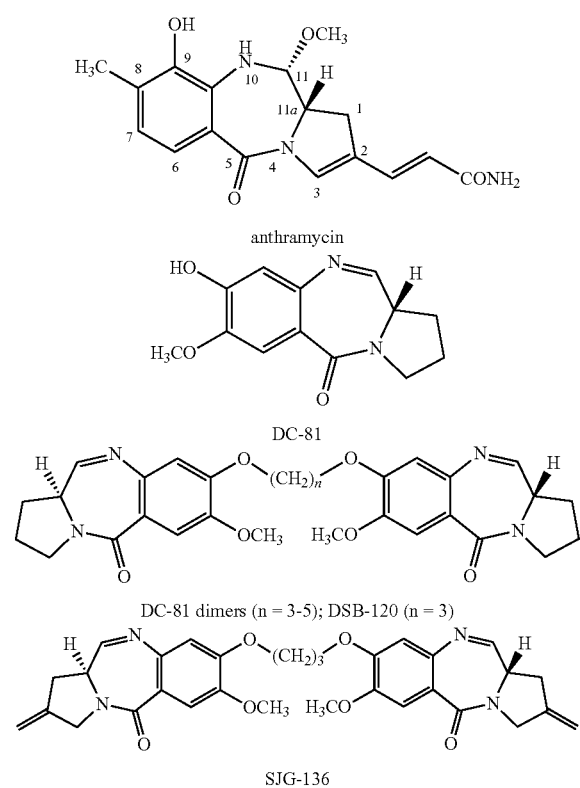

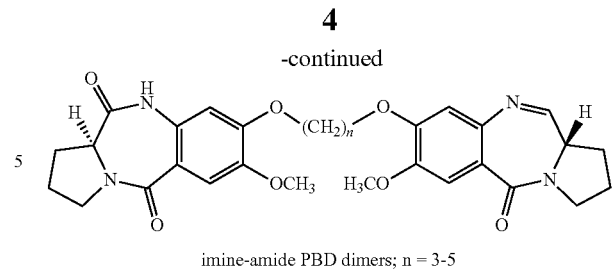

imine-amide PBD dimers; n = 3-5

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, O.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity (Kamal, A.; Srinivas, O.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide novel chalcone linked pyrrolo[2,1-c][1,4]benzodiazepine hybrids, useful as antitumour agents.

Yet another object of this invention is to provide a process for the preparation of novel chalcone linked pyrrolo[2,1-c][1,4]benzodiazepine hybrids.

SUMMARY OF THE INVENTION

Accordingly the present invention provides a novel chalcone linked pyrrolo[2,1-c][1,4]benzodiazepine hybrid of general A

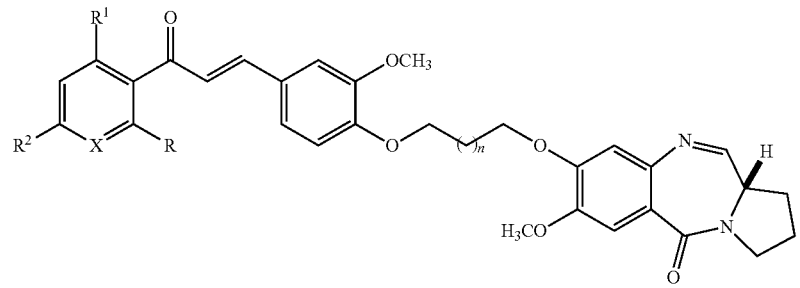

wherein R¹=OH, methyl, ethyl or phenyl; R²=H, OH or F; R=H or methyl; x=c or N; n=1-4

In an embodiment of the present invention the novel chalcone linked pyrrolo[2,1-c][1,4]benzodiazepine hybrid of general A is also represented as formula 6 and 10.

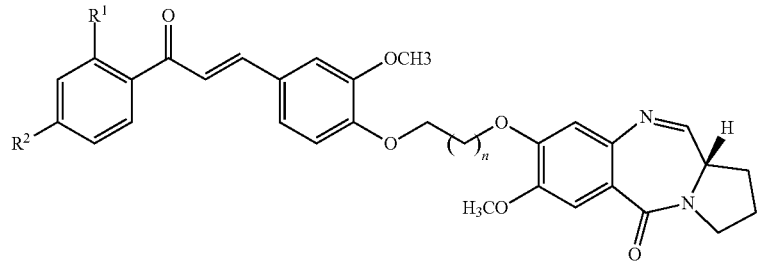

Formula 6a-i

R¹ = OH, R² = OH, F
n = 2,3,4,

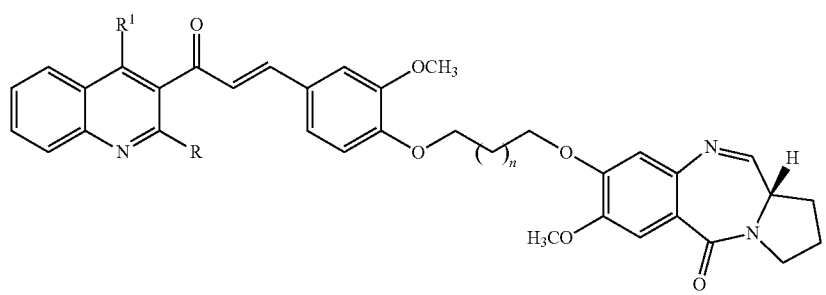

Formula 10a-I

R¹ = methyl, ethyl, phenyl
R = methyl
n = 1, 2, 3, 4,

In an embodiment of the present invention the novel chalcone linked pyrrolo[2,1-c][1,4]benzodiazepine hybrid as claimed in claim 1 is represented by the group of the following compounds:

7-Methoxy-8-{3-[1-(4-fluorophenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one(6a);

7-Methoxy-8-{4-[1-(4-fluorophenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one(6b);

7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6c);

7-Methoxy-8-{3-[1-(2-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6d);

7-Methoxy-8-{4-[1-(2-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6e);

7-Methoxy-8-{5-[1-(2-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6f);

7-Methoxy-8-{3-[1-(4-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6g);

7-Methoxy-8-{4-[1-(4-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6h);

7-Methoxy-8-{5-[1-(4-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6i);

7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one (10a);

7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one (10b);

7-Methoxy-8-{5-[3-(4-hydroxy-3-methoxyphenyl)-1-(2,4-dimethyl-3-quinolyl)-2-propen-1-one]pentyl}-oxy-(11aS)-1,2,3,11a-5H-pyrrolo[2,1-c][1,4]benzodiazepin-5-one (10c);

7-Methoxy-8-{6-[3-(4-hydroxy-3-methoxyphenyl)-1-(2,4-dimethyl-3-quinolyl)-2-propen-1-one]hexyl}-oxy-(11aS)-1,2,3,11a-5H-pyrrolo[2,1-c][1,4]benzodiazepin-5-one (10d);

7-Methoxy-8-{3-[3-(4-hydroxy-3-methoxyphenyl)-1-(2-methyl-4-phenyl-3-quinolyl)-2-propen-1-one]proyl}-oxy-(11aS)-1,2,3,11a-5H-pyrrolo[2,1-c][1,4]benzodiazepin-5-one (10e);

7-Methoxy-8-{4-[3-(4-hydroxy-3-methoxyphenyl)-1-(2-methyl-4-phenyl-3-quinolyl)-2-propen-1-one]butyl}-oxy-(11aS)-1,2,3,11a-5H-pyrrolo[2,1-c][1,4]benzodiazepin-5-one (10f);

7-Methoxy-8-{5-[3-(4-hydroxy-3-methoxyphenyl)-1-(2-methyl-4-phenyl-3-quinolyl)-2-propen-1-one]pentyl}-oxy-(11aS)-1,2,3,11a-5H-pyrrolo[2,1-c][1,4]benzodiazepin-5-one (10g);

7-Methoxy-8-{6-[3-(4-hydroxy-3-methoxyphenyl)-1-(2-methyl-4-phenyl-3-quinolyl)-2-propen-1-one]hexyl}-oxy-(11aS)-1,2,3,11a-5H-pyrrolo[2,1-c][1,4]benzodiazepin-5-one (10h);

7-Methoxy-8-{3-[3-(4-hydroxy-3-methoxyphenyl)-1-(2-methyl-4-ethyl-3-quinolyl)-2-propen-1-one]propyl}-oxy-(11aS)-1,2,3,11a-5H-pyrrolo[2,1-c][1,4]benzodiazepin-5-one (10i);

7-Methoxy-8-{4-[3-(4-hydroxy-3-methoxyphenyl)-1-(2-methyl-4-ethyl-3-quinolyl)-2-propen-1-one]butyl}-oxy-(11aS)-1,2,3,11a-5H-pyrrolo[2,1-c][1,4]benzodiazepin-5-one (10j);

7-Methoxy-8-{5-[3-(4-hydroxy-3-methoxyphenyl)-1-(2-methyl-4-ethyl-3-quinolyl)-2-propen-1-one]pentyl}-oxy-(11aS)-1,2,3,11a-5H-pyrrolo[2,1-c][1,4]benzodiazepin-5-one (10k);

7-Methoxy-8-{6-[3-(4-hydroxy-3-methoxyphenyl)-1-(2-methyl-4-ethyl-3-quinolyl)-2-propen-1-one]hexyl}-oxy-(11aS)-1,2,3,11a-5H-pyrrolo[2,1-c][1,4]benzodiazepin-5-one (10l);

In yet another embodiment the structural formula of the representative compounds of chalcone linked pyrrolo[2,1-c][1,4]benzodiazepine hybrid are:

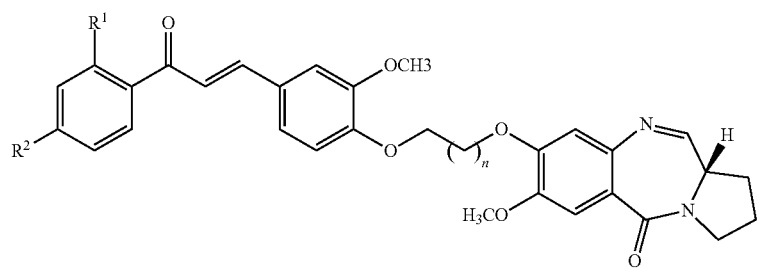

Formula 6a-i

R1 = OH, R2 = OH, F
n = 2,3,4

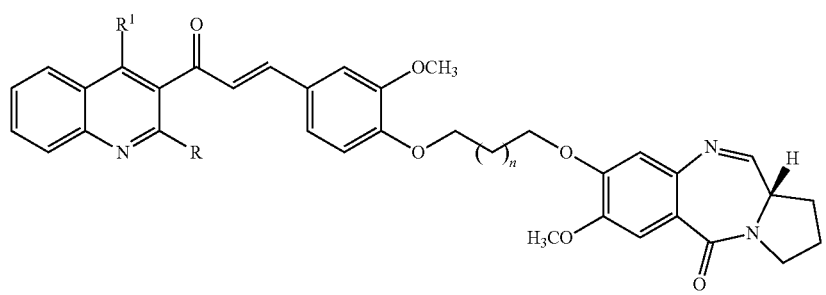

Formula 10a-I

R¹ = methyl, ethyl, phenyl
R = methyl
n = 1, 2, 3, 4,

In yet another embodiment the novel chalcone linked pyrrolo[2,1-c][1,4]benzodiazepine hybrid exhibits an in vitro anticancer/antitumour activity against human cancer cell lines selected from the group consisting of lung (NCI-H522), cervix (SiHa), breast (MDA-MB-435, Zr-75-1), colon (COLO-205), prostate (DU145, PC3) and oral (DWD, HT1080), melanoma (LOX IMVI, VACC-62) cell lines.

In yet another embodiment the concentration of chalcone linked pyrrolo[2,1-c][1,4]benzodiazepine hybrid used for in vitro activity against COLO-205 for IC50 is in the range of 16 to 80 μm, at an exposure period of at least 48 hrs.

In yet another embodiment the concentration of chalcone linked pyrrolo[2,1-c][1,4]benzodiazepine hybrids used for in vitro activity against DU145 for IC50 is in the range of 16 to 80 μm, at an exposure period of at least 48 hrs.

In yet another embodiment the concentration of chalcone linked pyrrolo[2,1-c][1,4]benzodiazepine hybrids used for in vitro activity against NCI-H522 for IC50 is in the range of 6 to 80 μm, at an exposure period of at least 48 hrs.

In yet another embodiment the concentration of chalcone linked pyrrolo[2,1-c][1,4]benzodiazepine hybrids used for in vitro activity against COLO-205 for IC50 is preferably in the range of 19 to 40 μm, at an exposure period of at least 48 hrs.

In yet another embodiment the concentration of chalcone linked pyrrolo[2,1-c][1,4]benzodiazepine hybrids used for in vitro activity against LOXIMVI for IC50 is in the range of 5 to 30 μm, at an exposure period of at least 48 hrs.

In yet another embodiment the concentration of chalcone linked pyrrolo[2,1-c][1,4]benzodiazepine hybrids used for in vitro activity against VACC-62 for IC50 is in the range of 7 to about 54 μm, at an exposure period of at least 48 hrs.

In yet another embodiment the concentration of chalcone linked pyrrolo[2,1-c][1,4]benzodiazepine hybrids used for in vitro activity against MDA-MB-435 for IC50 is in the range of 9 to about 69 μm, at an exposure period of at least 48 hrs.

In yet another embodiment the concentration of chalcone linked pyrrolo[2,1-c][1,4]benzodiazepine hybrids used for in vitro activity against SiHa for IC50 is in the range of 29 to about 80 μm, at an exposure period of at least 48 hrs.

In yet another embodiment the concentration of chalcone linked pyrrolo[2,1-c][1,4]benzodiazepine hybrids used for in vitro activity against Zr-75-1 for IC50 is in the range of 24 to about 80 μm, at an exposure period of at least 48 hrs.

In yet another embodiment Chalcone linked pyrrolo[2,1-c][1,4]benzodiazepine hybrids as claimed in claims 1&2, wherein the concentration of the compound used for in vitro activity against DWD for IC50 is in the range of 6 to 80 μm, at an exposure period of at least 48 hrs.

In yet another embodiment Chalcone linked pyrrolo[2,1-c][1,4]benzodiazepine hybrid as claimed in claims 1&2, wherein the concentration of the compound used for in vitro activity against HoP62 for IC50 is in the range of 13 to 40 μm, at an exposure period of at least 48 hrs.

In yet another embodiment Chalcone linked pyrrolo[2,1-c][1,4]benzodiazepine hybrid as claimed in claims 1&2, wherein the concentration of the compound used for in vitro activity against HT1080 for IC50 is in the range of 6 to 30 μm, at an exposure period of at least 48 hrs.

In yet another embodiment Chalcone linked pyrrolo[2,1-c][1,4]benzodiazepine hybrid as claimed in claims 1&2, wherein the concentration of the compound used for in vitro activity against MCF7 for IC50 is in the range of 27 to about 80 μm, at an exposure period of at least 48 hrs.

In yet another embodiment Chalcone linked pyrrolo[2,1-c][1,4]benzodiazepine hybrid as claimed in claims 1&2, wherein the concentration of the compound used for in vitro activity against PC3 for IC50 is in the range of 9 to about 80 μm, at an exposure period of at least 48 hrs.

The present invention further provides a pharmaceutical composition comprising chalcone linked pyrrolo[2,1-c][1,4] benzodiazepine hybrid, its derivatives, analogues, salts or mixture thereof optionally with pharmaceutically acceptable carriers, adjuvants and additives.

In yet another embodiment the chalcone linked pyrrolo[2,1-c][1,4]benzodiazepine hybrid used is represented by a general formula 6 and 10

Formula 6

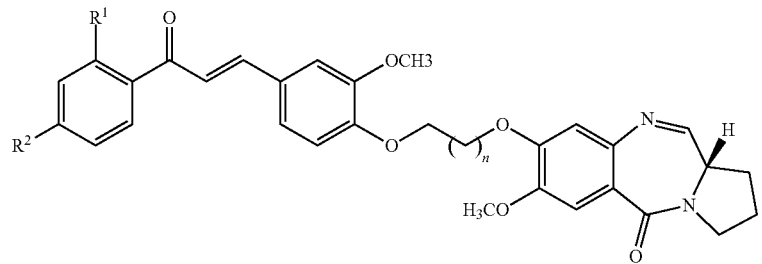

$R^1$ = hydroxyl; $R^2$ = hydroxyl, fluorine.
n = 2,3,4,

Formula 10

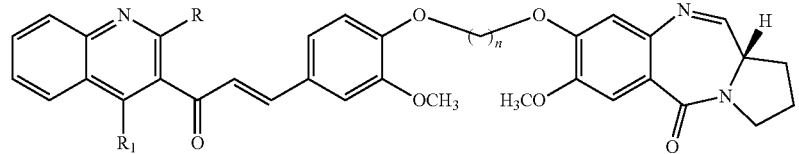

n = 3, 4, 5, 6
$R^1$ = methyl, ethyl, phenyl
R = methyl

The present invention further provides a process for the preparation of chalcone linked pyrrolo[2,1-c][1,4]benzodiazepine hybrid of formula 6 and 10, Formula 6

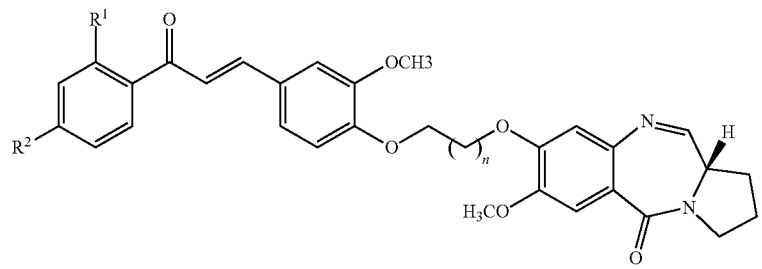

$R^1$ = hydroxyl; $R^2$ = hydroxyl, flourine.
n = 2,3,4

Formula 10

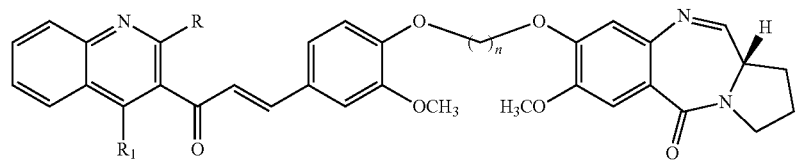

n = 3, 4, 5, 6
$R^1$ = methyl, ethyl, phenyl
R = methyl and the said process comprising the steps of:
a) Reacting (2S)—N-[4-(n-bromoalkyl)oxy-5-methoxy-2-nitrobenzoyl]pyrrolidine-2-carboxaldehyde diethylthioacetal of formula 2

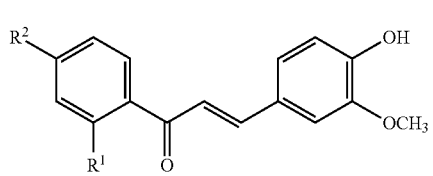

with chalcone derivatives selected from the compounds of formulas 3 and 7

Formula 3

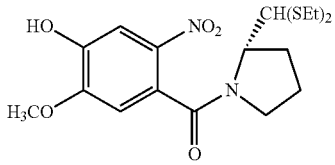

Formula 7

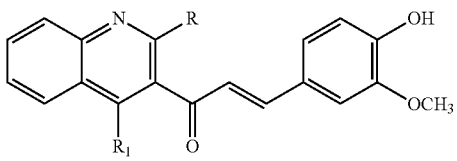

$R^1$ = Hydroxy; $R^2$ = Hydroxy, Flourine
R = methyl, ethyl, phenyl R1
R = methyl in the presence of a base selected from an inorganic base selected from a group of K2CO3 and CH$_3$COCH$_3$ or, in an organic solvent, under refluxing temperature to obtain the resultant nitro compounds of formulas 4 and 8.

Formula 4

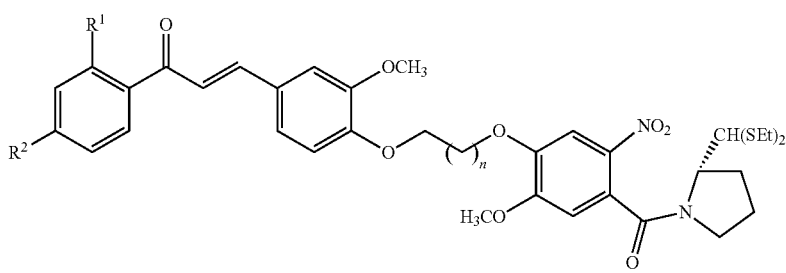

$R^1$ = hydroxyl; $R^2$ = hydroxyl, flourine.
n = 3, 4,5

Formula 8

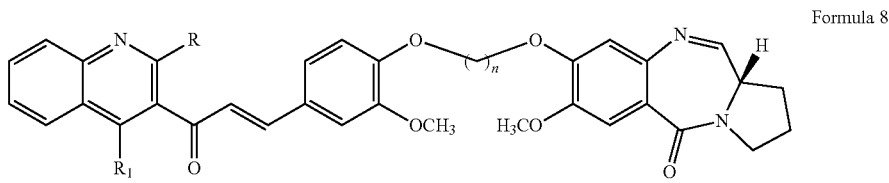

n = 3, 4, 5, 6
$R^1$ = methyl, ethyl, phenyl
R = methyl b) Reducing the above said nitro compounds of formula 4 and 8 obtained in step (a) with SnCl$_2$.2H$_2$O in an organic solvent, under reflux temperature and isolating the corresponding amino compounds of formula 5 and 9 respectively Formula 5

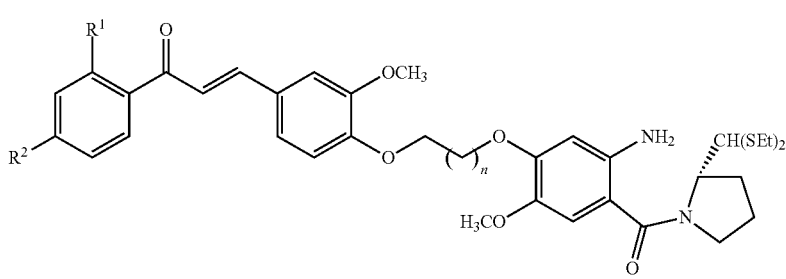

R¹ = hydroxyl; R² = hydroxyl, flourine.
n = 2, 3, 4,

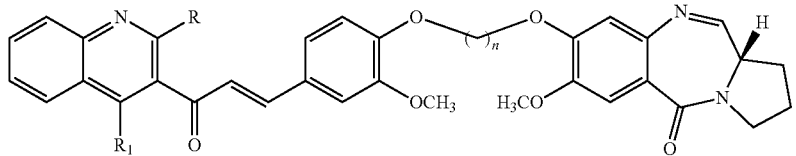

Formula 9 n = 3, 4, 5, 6
R¹ = methyl, ethyl, phenyl
R = methyl c) Reacting the above said amino compounds of formula 5 and 9 obtained is step (b) with a deprotecting agent in presence of an organic solvent by known method to obtain the desired compounds of formula 6 and 10.

In yet another embodiment the inorganic base used in steps (a) is potassium carbonate.

In yet another embodiment the aprotic organic solvent used in step (a) is acetone and acetonitrile In yet another embodiment the organic solvent used in step (c) is acetonitrile in yet another embodiment the organic solvent used in step (b) is an alcohol selected from methanol and ethanol.

In yet anther embodiment the compounds of formula 6a-i and 10a-l obtained are represented by a group of the following compounds:

7-Methoxy-8-{3-[1-(4-fluorophenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one(6a);

7-Methoxy-8-{4-[1-(4-fluorophenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one(6b);

7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6c);

7-Methoxy-8-{3-[1-(2-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6d);

7-Methoxy-8-{4-[1-(2-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6e);

7-Methoxy-8-{5-[1-(2-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6f);

7-Methoxy-8-{3-[1-(4-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6g);

7-Methoxy-8-{4-[1-(4-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6h);

7-Methoxy-8-{5-[1-(4-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6i);

7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one (10a);

7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one (10b);

7-Methoxy-8-{5-[3-(4-hydroxy-3-methoxyphenyl)-1-(2,4-dimethyl-3-quinolyl)-2-propen-1-one]pentyl}-oxy-(11aS)-1,2,3,11a-5H-pyrrolo[2,1-c][1,4]benzodiazepin-5-one (10c);

7-Methoxy-8-{6-[3-(4-hydroxy-3-methoxyphenyl)-1-(2,4-dimethyl-3-quinolyl)-2-propen-1-one]hexyl}-oxy-(11aS)-1,2,3,11a-5H-pyrrolo[2,1-c][1,4]benzodiazepin-5-one (10d);

7-Methoxy-8-{3-[3-(4-hydroxy-3-methoxyphenyl)-1-(2-methyl-4-phenyl-3-quinolyl)-2-propen-1-one]propyl}-oxy-(11aS)-1,2,3,11a-5H-pyrrolo[2,1-c][1,4]benzodiazepin-5-one (10e);

7-Methoxy-8-{4-[3-(4-hydroxy-3-methoxyphenyl)-1-(2-methyl-4-phenyl-3-quinolyl)-2-propen-1-one]butyl}-oxy-(11aS)-1,2,3,11a-5H-pyrrolo[2,1-c][1,4]benzodiazepin-5-one (10f);

7-Methoxy-8-{5-[3-(4-hydroxy-3-methoxyphenyl)-1-(2-methyl-4-phenyl-3-quinolyl)-2-propen-1-one]pentyl}-oxy-(11aS)-1,2,3,11a-5H-pyrrolo[2,1-c][1,4]benzodiazepin-5-one (10g);

7-Methoxy-8-{6-[3-(4-hydroxy-3-methoxyphenyl)-1-(2-methyl-4-phenyl-3-quinolyl)-2-propen-1-one]hexyl}-oxy-(11aS)-1,2,3,11a-5H-pyrrolo[2,1-c][1,4]benzodiazepin-5-one (10h);

7-Methoxy-8-{3-[3-(4-hydroxy-3-methoxyphenyl)-1-(2-methyl-4-ethyl-3-quinolyl)-2-propen-1-one]propyl}-oxy-(11aS)-1,2,3,11a-5H-pyrrolo[2,1-c][1,4]benzodiazepin-5-one (10i);

7-Methoxy-8-{4-[3-(4-hydroxy-3-methoxyphenyl)-1-(2-methyl-4-ethyl-3-quinolyl)-2-propen-1-one]butyl}-oxy-(11aS)-1,2,3,11a-5H-pyrrolo[2,1-c][1,4]benzodiazepin-5-one (10j);

7-Methoxy-8-{5-[3-(4-hydroxy-3-methoxyphenyl)-1-(2-methyl-4-ethyl-3-quinolyl)-2-propen-1-one]pentyl}-oxy-(11aS)-1,2,3,11a-5H-pyrrolo[2,1-c][1,4]benzodiazepin-5-one (10k);

7-Methoxy-8-{6-[3-(4-hydroxy-3-methoxyphenyl)-1-(2-methyl-4-ethyl-3-quinolyl)-2-propen-1-one]hexyl}-oxy-(11aS)-1,2,3,11a-5H-pyrrolo[2,1-c][1,4]benzodiazepin-5-one (10l);

In still anther embodiment the chalcone linked pyrrolo[2,1-c][1,4]benzodiazepine hybrid of formula 6a-m exhibits an in vitro anticancer/antitumour activity against human cancer cell lines selected from the group consisting of lung, cervix, breast, colon, prostate and oral cell lines.

DETAILED DESCRIPTION OF THE INVENTION

Accordingly, the present invention provides a process for preparation of pyrrolo[2,1-c][1,4]benzodiazepine hybrids of formula 6a-i and 10a-l

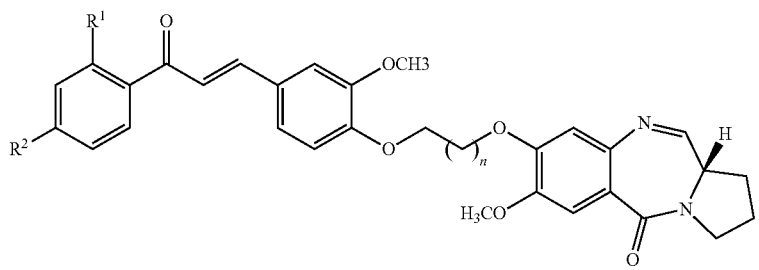

Formula 6

R¹ = hydroxyl; R² = hydroxyl, flourine.
N = 2, 3, 4

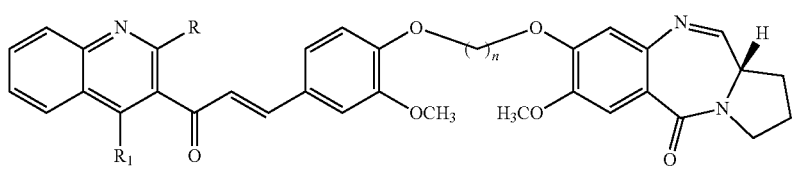

Formula 10 n = 3, 4, 5, 6
R¹ = methyl, ethyl, phenyl
R = methyl which comprises reacting (2 or 4-substituted phenyl)-3-(4-hydroxy-3-methoxyphenyl)-2-propen-1-one] of formula 3 and {3-(4-hydroxy-3-methoxyphenyl)-1-(2-methyl-4-alkyl/aryl-3-quinolyl)-2-propen-1-one of formula 7 with (2S)—N-[(n-bromoalkyloxy)-3-methoxy-2-nitrobenzoyl]pyrrolidine-2-carboxaldehyde diethylthioacetal of formula 2 in presence of $CH_3COCH_3/K_2CO_3$ for a period of 48 h and isolating (2S)—N-{4-n-[1-(2 or 4-substituted phenyl)-3-(4-hydroxy-3-methoxyphenyl)-2-propen-1-one]alkyl]oxy]-5-methoxy-2-nitrobenzoyl}pyrrolidine-2-carboxaldehyde diethylthioacetal and (2S)—N-{n-(4-hydroxy-3-methoxyphenyl)-1-(2-methyl-4-alkyl/aryl-3-quinolyl)-2-propen-1-one]alkyl]oxy-5-methoxy-2-nitrobenzoyl}pyrrolidine-2-carboxaldehyde diethylthioacetal of formula 4a-i and 8a-l respectively. Reducing the above nitro compounds of formula 4a-i and 8a-l with $SnCl_2.2H_2O$ in presence of organic solvent with reflux temperature, resulting with the formation of (2S)—N-{4-[n-[1-(2 or 4-substituted phenyl)-3-(4-hydroxy-3-methoxyphenyl)-2-propen-1-one]alkyl]oxy]-5-methoxy-2-aminobenzoyl}pyrrolidine-2-carboxaldehyde diethyl thioacetal and (2S)—N-{n-(4-hydroxy-3-methoxyphenyl)-1-(2-methyl-4-alkyl/aryl-3-quinolyl)-2-propen-1-one]alkyloxy-5-methoxy-2-aminobenzoyl}pyrrolidine-2-carboxaldehyde diethylthioacetal of formula 5a-i and 9a-l respectively. Reacting the above said amino compounds of formula 5a-i and 9a-l with known deprotecting agents in a conventional manner to give novel pyrrolo[2,1-c][1,4]benzodiazepine hybrids of formula 6a-i and 10a-l, where 'n' is as stated above. The precursors, chalcone side chains of formula 7 & 3 have been prepared by simple known methods. (Mei Liu, Prapon Wilairat, and Mei-Lin Go, *J. Med. Chem.* 2001, 44, 4443-4452). And other derivative (2S)—N-(4-hydroxy-5-methoxy-2-nitrobenzoyl)pyrrolidine-2-carboxaldehyde diethylthioacetal of formula 1 (Thurston, D. E.; Morris, S. J.; Hartley, J. A. *Chem. Commun.* 1996, 563-565) have been prepared by literature methods.

Some representative compounds of the present inventions are given below.

(6a) 7-Methoxy-8-{3-[1-(4-fluorophenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one;

(6b) 7-Methoxy-8-{4-[1-(4-fluorophenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one;

(6c) 7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one;

(10a) 7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one (10b) 7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one (10c) 7-Methoxy-8-{5-[3-(4-hydroxy-3-methoxyphenyl)-1-(2,4-dimethyl-3-quinolyl)-2-propen-1-one]pentyl}-oxy-(11aS)-1,2,3,11a-5H-pyrrolo[2,1-c][1,4]benzodiazepin-5-one (10d) 7-Methoxy-8-{6-[3-(4-hydroxy-3-methoxyphenyl)-1-(2,4-dimethyl-3-quinolyl)-2-propen-1-one]hexyl}-oxy-(11aS)-1,2,3,11a-5H-pyrrolo[2,1-c][1,4]benzodiazepin-5-one The process for the preparation of new pyrrolo[2,1-c][1,4]benzodiazepine hybrids is disclosed and claimed in our co-pending Indian Patent Application No. 518/DEL/2008.

These new analogues of pyrrolo[2,1-c][1,4]benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in scheme-1 and scheme-2, which comprise:

1. The ether linkage at C-8 position of DC-81 intermediates with [1-(4-fluorophenyl)-3-(4-hydroxy-3-methoxyphenyl)-2-propen-1-one] and 3-(4-hydroxy-3-methoxyphenyl)-1-(4-phenyl-3-quinolyl)-2-propen-1-one moiety.
2. Refluxing the reaction mixtures for 48 h.
3. Synthesis of C-8 linked PBD antitumour antibiotic hybrid imines.
4. Purification by column chromatography using different solvents like ethyl acetate, hexane, chloroform and methanol.

Scheme-1
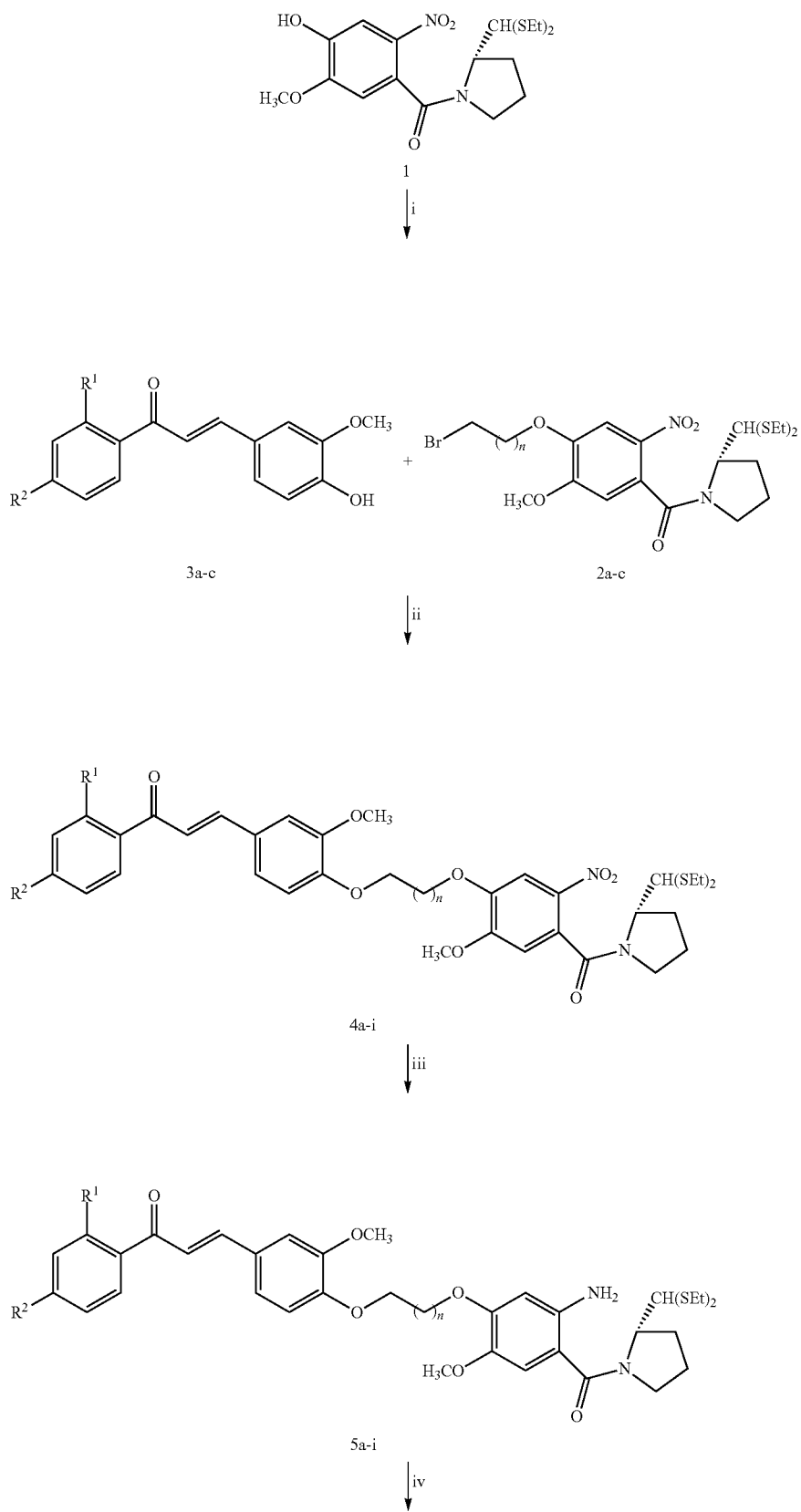

-continued
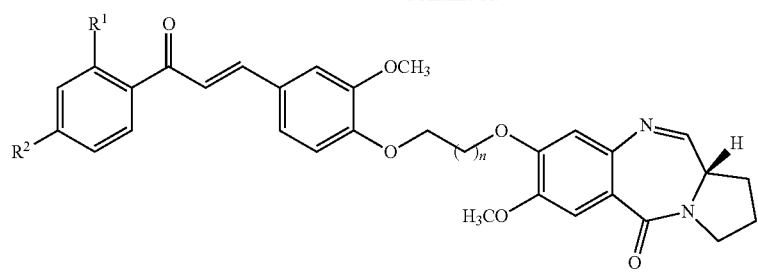
6a-i
$R^1$ = OH, $R^2$ = OH, F
n = 2-4
Reagents and conditions: (i) dibromoalkanes, $K_2CO_3$, acetone, 48 h, refllux, 94-96%; (ii) acetone 48 h, refllux, 94-96%; (iii) $SnCl_2 \cdot 2H_2O$, MeOH, 2 h, reflux, 85-87%; (iv) $HgCl_2$—$CaCO_3$, $CH_3CN$—$H_2O$ (4:1), 12 h, rt, 68-71%.
Scheme-2
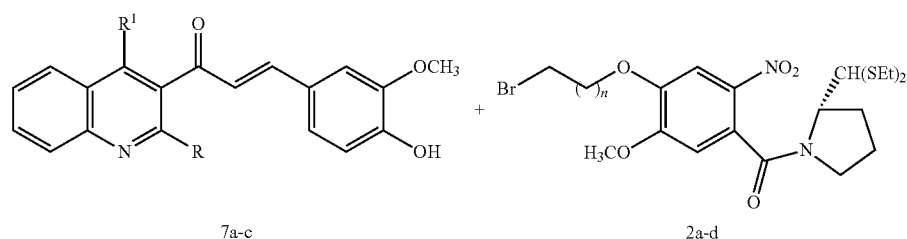
7a-c       2a-d
↓ i
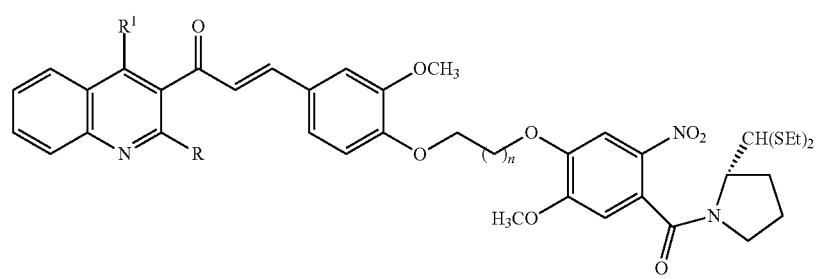
8a-I
 ii
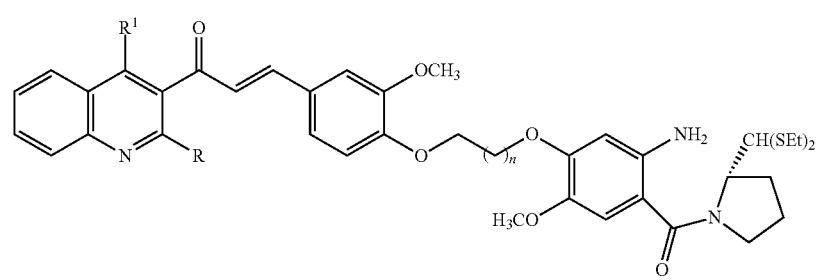
9a-I
 iii -continued

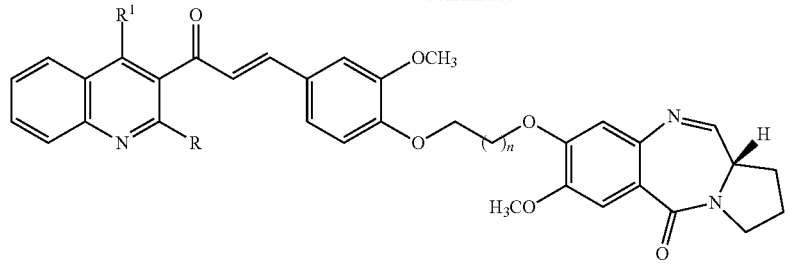

10a-I $R^1$ = Methyl, Ethyl, Phenyl
R = Methyl
n = 2-5
Reagents and conditions: (i) $K_2CO_3$, acetone, 48 h, refllux, 94-96%; (ii) $SnCl_2 \cdot 2H_2O$, MeOH, 2 h, reflux, 85-87%;
(iii) $HgCl_2$—$CaCO_3$, $CH_3CN$—$H_2O$ (4:1), 12 h, rt, 68-71%.

The following examples are given by way of illustration and therefore should not be construed to the present limit of the scope of invention.

Example—1

(2S)—N-{4-[3-[1-(4-fluorophenyl)-3-(4-hydroxy-3-methoxyphenyl)-2-propen-1-one]propyl]oxy]-5-methoxy-2-nitrobenzoyl}pyrrolidine-2-carboxaldehydediethylthioacetal (4a)

To a solution of compound (2S)—N-[4-(3-bromopropyloxy-5-methoxy-2-nitrobenzoyl]pyrrolidine-2-carboxaldehyde diethylthioacetal 2a (521 mg, 1.0 mmol) in dry acetone (15 ml) was added, 1-(4-fluorophenyl)-3-(4-hydroxy-3-methoxyphenyl)-2-propen-1-one 3a (272 mg, 1.0 mmol) followed by anhydrous $K_2CO_3$ (690 mg, 3.0 mmol) and the reaction mixture was refluxed for 48 hrs. After the completion of the reaction as indicated by TLC, potassium carbonate was removed by suction filtration and the solvent was removed under vacuum. The crude product thus obtained was purified by column chromatography using ethyl acetate-hexane (1:1) as eluant to afford pure compound 4a as yellow liquid (650 mg, 91%).

$^1$H NMR ($CDCl_3$): δ1.30-1.40 (m, 6H), 1.61-2.30 (m, 4H), 2.65-2.85 (m, 4H), 3.19-3.26 (m, 6H), 3.65-3.95 (m, 3H), 4.05-4.15 (m, 2H), 4.63-4.70 (m, 1H), 4.81-4.83 (d, 1H, J=3.77 HZ), 6.71-6.96 (m, 1H), 7.09-7.40 (m, 1H), 7.61-7.73 (m, 1H), 7.95-8.03 (d, 1H, J=7.6 Hz), MS (FAB) 712 [M+H]$^+$.

(2S)—N-{4-[4-(1-(4-fluorophenyl)-3-(4-hydroxy-3-methoxyphenyl)-2-propen-1-one]propyl]oxy]-5-methoxy-2-aminobenzoyl}pyrrolidine-2-carboxaldehyde diethyl thioacetal (5a)

The compound 4a (715 mg, 1 mmol) dissolved in methanol (20 ml) and added $SnCl_2 \cdot 2H_2O$ (1.125 g, 5.0 mmol) was refluxed for 2 h or until the TLC indicated that reaction was complete. The methanol was evaporated under vacuum and the aqueous layer was then adjusted to pH 8 with 10% $NaHCO_3$ solution and then extracted with ethyl acetate (2×30 ml). The combined organic phase was dried over $Na_2SO_4$ and evaporated under vacuum to afford the amino diethyl thioacetal, 5a, which, due to potential stability problems, was used directly in the next step (680 mg, 95%).

7-Methoxy-8-{3-[1-(4-fluorophenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6a).

A solution of 5a (680 mg, 1.0 mmol), $HgCl_2$ (871 mg, 2.5 mmol) and $CaCO_3$ (250 mg, 2.5 mmol) in acetonitrile-water (4:1) was stirred at room temperature for 12 h until the completion of the reaction as shown by TLC (EtOAc). The organic layer was evaporated in vacuum and the residue was diluted with EtOAc. To this, saturated $NaHCO_3$ was added slowly at room temperature and the mixture was filtered through a celite bed and washed with ethyl acetate. The filtrate was evaporated in vacuum to get crude compound 6a, which was further purified by column chromatography on silica gel eluting first with ethyl acetate to remove traces of mercuric salts and then with $CHCl_3$:methanol (9:1) (356 mg, 63%).

$^1$H NMR ($CDCl_3$): delta 1.17-1.36 m, 6H), 1.82-2.26 (m, 6H), 2.45-2.75 (m, 4H), 2.98-3.15 (m, 4H), 3.26-3.76 (m, 4H), 3.85 (s, 3H), 4.00-4.20 (m, 2H), 4.32-4.51 (m, 1H), 6.77-7.21 (m, 1H), 7.48-7.82 (m, 3H), 7.87-7.92 (d, 1H, J=8.59 Hz), 8.12-8.22 (m, 2H), 8.33-8.35 (m, 3H), 8.68-8.75 (d, 1H, J=8.59 Hz); MS (FAB) 558 [M+H]$^+$ Example—2

(2S)—N-{4-[4-[1-(4-fluorophenyl)-3-(4-hydroxy-3-methoxyphenyl)-2-propen-1-one]butyl]oxy]-5-methoxy-2-nitrobenzoyl}pyrrolidine-2-carboxaldehydediethylthioacetal (4b)

The compound 4b has been prepared according to the method described for the compound 4a by employing the compound (2S)—N-[4-(4-bromobutyloxy-5-methoxy-2-nitrobenzoyl]pyrrolidine-2-carboxaldehyde diethylthioacetal 2b (535 mg, 1.0 mmol) followed by anhydrous $K_2CO_3$ (690 mg, 3.0 mmol) and 4-fluoro substituted chalcone 3a (272 mg, 1.0 mmol) to afford the compound 4b (670 mg, 91%).

$^1$H NMR ($CDCl_3$): δ1.30-1.40 (m, 6H), 1.61-2.30 (m, 4H), 2.65-2.85 (m, 4H), 3.19-3.26 (m, 6H), 3.65-3.95 (m, 3H), 4.05-4.15 (m, 2H), 4.63-4.70 (m, 1H), 4.81-4.83 (d, 1H, J=3.77 HZ), 6.71-6.96 (m, 1H), 7.09-7.40 (m, 1H), 7.61-7.73 (m, 1H), 7.95-8.03 (d, 1H, J=7.6 Hz), MS (FAB) 726 [M+H]$^+$.

(2S)—N-{4-[4-[1-(4-fluorophenyl)-3-(4-hydroxy-3-methoxyphenyl)-2-propen-1-one]butyl]oxy]-5-methoxy-2-aminobenzoyl}pyrrolidine-2-carboxaldehydediethyl thioacetal (5b)

The compound 5b has been prepared according to the method described for the compound 4a by employing compound 4b (725 mg, 1.0 mmol) to afford compound 5b (660 mg, 95%), which, due to potential stability problems, was used directly in the next step.

7-Methoxy-8-{4-[4-1-(4-fluorophenyl)-3-(4-hydroxy-3-methoxyphenyl)-2-propen-1-one]butyl}-oxy}-(11aS)-1,2,3,11a-5H-pyrrolo[2,1-c][1,4]benzodiazepin-5-one (6b)

The compound 6b was prepared according to the method described for the compound 6a employing the compound 5b (695 mg, 1.0 mmol) to afford the compound 6b (400 mg, 68%).

$^1$H NMR (CDCl$_3$): δ 1.18-1.38 m, 6H), 1.82-2.26 (m, 4H), 2.45-2.75 m, 4H), 2.98-3.15 (m, 4H), 3.26-3.76 (m, 4H), 3.85 (s, 3H), 4.00-4.20 (m, 2H), 4.32-4.51 (m, 1H), 6.78-7.22 (m, 1H), 7.49-7.84 (m, 3H), 7.86-7.93 (d, 1H, J=8.59 Hz), 8.13-8.24 (m, 2H), 8.32-8.35 (m, 3H), 8.69-8.76 (d, 1H, J=8.58 Hz); MS (FAB) 572 [M+H]$^+$

Example—3

(2S)—N-{4-[5-[1-(4-fluorophenyl)-3-(4-hydroxy-3-methoxyphenyl)-2-propen-1-one]pentyl]oxy]-5-methoxy-2-nitrobenzoyl}pyrrolidine-2-carboxaldehydediethylthioacetal (4c)

The compound 4c has been prepared according to the method described for the compound 4a by employing the compounds (2S)—N-[4-(5-bromopentyloxy-5-methoxy-2-nitrobenzoyl]pyrrolidine-2-carboxaldehyde diethylthioacetal 2c (549 mg, 1.0 mmol) followed by anhydrous K$_2$CO$_3$ (690 mg, 3.0 mmol) and 4-fluoro substituted chalcone 3a (272 mg, 1.0 mmol) to afford the compound 4c (685 mg, 92%).

$^1$H NMR (CDCl$_3$): delta 1.30-1.40 (m, 6H), 1.61-2.30 (m, 4H), 2.65-2.85 (m, 4H), 3.19-3.26 (m, 6H), 3.65-3.95 (m, 3H), 4.05-4.15 (m, 2H), 4.63-4.70 (m, 1H), 4.81-4.83 (d, 1H, J=3.77 HZ), 6.71-6.96 (m, 1H), 7.09-7.40 (m, 1H), 7.61-7.73 (m, 1H), 7.95-8.03 (d, 1H, J=7.6 Hz), MS (FAB) 740 [M+H]$^+$.

(2S)—N-{4-[4-[1-(4-fluorophenyl)-3-(4-hydroxy-3-methoxyphenyl)-2-propen-1-one]pentyl]oxy]-5-methoxy-2-aminobenzoyl}pyrrolidine-2-carboxaldehyde diethyl thioacetal (5c)

The compound 5c has been prepared according to the method described for the compound 4a by employing compound 4c (740 mg, 1.0 mmol) to afford compound 5c (670 mg, 94%), which, due to potential stability problems, was used directly in the next step.

7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1,-c][1,4]benzodiazepin-5-one (6c)

The compound 6c was prepared according to the method described for the compound 6a employing the compound 5c (710 mg, 1.0 mmol) to afford the compound 6c (415 mg, 70%).

$^1$H NMR (CDCl$_3$): δ1.19-1.38 m, 6H), 1.82-2.26 (m, 4H), 2.45-2.75 m, 4H), 2.98-3.15 (m, 4H), 3.26-3.76 (m, 4H), 3.85 (s, 3H), 4.00-4.20 (m, 2H), 4.32-4.51 (m, 1H), 6.76-7.23 (m, 1H), 7.49-7.83 (m, 3H), 7.87-7.92 (d, 1H, J=8.59 Hz), 8.12-8.22 (m, 2H), 8.33-8.35 (m, 3H), 8.68-8.75 (d, 1H, J=8.60 Hz); MS (FAB) 586 [M+H]$^+$.

Example—4

2S)—N-{4-[3-[1-(2-hydroxyphenyl)-3-(4-hydroxy-3-methoxyphenyl)-2-propen-1-one]propyl]oxy]-5-methoxy-2-nitrobenzoyl}pyrrolidine-2-carboxaldehyde diethylthioacetal (4d)

The compound 4d has been prepared according to the method described for the compound 4a by employing the compounds (2S)—N44-(3-bromopropyloxy-5-methoxy-2-nitrobenzoyl]pyrrolidine-2-carboxaldehyde 2a diethylthioacetal (521 mg, 1.0 mmol) followed by anhydrous K$_2$CO$_3$ (690 mg, 3.0 mmol) and 2-hydroxy substituted chalcone 3b (270 mg, 1.0 mmol) to afford the compound 4d (620 mg, 87%).

$^1$H NMR (CDCl$_3$): δ1.31-1.41 (m, 6H), 1.60-2.32 (m, 4H), 2.64-2.86 (m, 4H), 3.18-3.25 (m, 6H), 3.64-3.96 (m, 3H), 4.06-4.17 (m, 2H), 4.63-4.72 (m, 1H), 4.83-4.84 (d, 1H, J=3.79 HZ), 6.72-6.98 (m, 1H), 7.08-7.41 (m, 1H), 7.62-7.74 (m, 1H), 7.96-8.03 (d, 1H, J=7.68 Hz), MS (FAB) 710 [M+H]$^+$.

(2S)—N-{4-[4-(1-(2-hydroxyphenyl)-3-(4-hydroxy-3-methoxyphenyl)-2-propen-1-one]propyl]oxy]-5-methoxy-2-aminobenzoyl}pyrrolidine-2-carboxaldehyde diethyl thioacetal (5d)

The compound 5d has been prepared according to the method described for the compound 5a by employing compound 4d (710 mg, 1.0 mmol) to afford compound 5d (630 mg, 92%), which, due to potential stability problems, was used directly in the next step.

7-Methoxy-8-{4-[4-1-(4-fluorophenyl)-3-(4-hydroxy-3-methoxyphenyl)-2-propen-1-one]propyl-oxy}-(11aS)-1,2,3,11a-5H-pyrrolo[2,1-c][1,4]benzodiazepin-5-one (6d)

The compound 6d was prepared according to the method described for the compound 6a employing the compound 5d (680 mg, 1.0 mmol) to afford the compound 6d (400 mg, 71%).

$^1$H NMR (CDCl$_3$): δ 1.18-1.38 (m, 6H), 1.82-2.26 (m, 4H), 2.45-2.75 (m, 4H), 2.98-3.15 (m, 4H), 3.26-3.76 (m, 4H), 3.85 (s, 3H), 4.00-4.20 (m, 2H), 4.32-4.51 (m, 1H), 6.78-7.22 (m, 1H), 7.49-7.84 (m, 3H), 7.86-7.93 (d, 1H, J=8.59 Hz), 8.13-8.24 (m, 2H), 8.32-8.35 (m, 3H), 8.69-8.76 (d, 1H, J=8.58 Hz); MS (FAB) 556 [M+H]$^+$

Example—5

(2S)—N-{4-[4-[1-(4-hydroxyphenyl)-3-(4-hydroxy-3-methoxyphenyl)-2-propen-1-one]butyl]oxy]-5-methoxy-2-nitrobenzoyl}pyrrolidine-2-carboxaldehydediethylthioacetal (4e)

The compound 4e has been prepared according to the method described for the compound 4a by employing the compounds (2S)—N-[4-(4-bromobutyloxy-5-methoxy-2-nitrobenzoyl]pyrrolidine-2-carboxaldehyde diethylthioacetal 2b (535 mg, 1.0 mmol) and 4-hydroxy substituted chalcone 3b (270 mg, 1.0 mmol) to afford the compound 4e (640 mg, 88%).

$^1$H NMR (CDCl$_3$): δ 1.32-1.40 (m, 6H), 1.63-2.31 (m, 4H), 2.64-2.86 (m, 4H), 3.18-3.25 (m, 6H), 3.63-3.94 (m, 3H), 4.07-4.16 (m, 2H), 4.64-4.71 (m, 1H), 4.82-4.84 (d, 1H, J=3.79 HZ), 6.72-6.89 (m, 1H), 7.07-7.38 (m, 1H), 7.63-7.75 (m, 1H), 7.93-8.06 (d, 1H, J=7.75 Hz), MS (FAB) 724 [M+H]$^+$.

(2S)—N-{4-[4-[1-(4-hydroxyphenyl)-3-(4-hydroxy-3-methoxyphenyl)-2-propen-1-one]butyl]oxy]-5-methoxy-2-aminobenzoyl}pyrrolidine-2-carboxaldehyde diethylthioacetal (5e)

The compound 5e has been prepared according to the method described for the compound 4a by employing compound 4e (725 mg, 1.0 mmol) to afford compound 5e (645 mg, 91%), which, due to potential stability problems, was used directly in the next step.

7-Methoxy-8-{3-[1-(4-hydroxyphenyl)-3-(4-hydroxy-3-methoxyphenyl)-2-propen-1-one]butyl}-oxy-(11aS)-1,2,3,11a-5H-pyrrolo[2,1-][1,4]benzodiazepin-5-one (6e)

The compound 6e was prepared according to the method described for the compound 6a employing the compound 5e (695 mg, 1.0 mmol) to afford the compound 6e (390 mg, 68%).

$^1$H NMR (CDCl$_3$): delta 1.17-1.36 (m, 6H), 1.82-2.26 (m, 6H), 2.45-2.75 (m, 4H), 2.98-3.15 (m, 4H), 3.26-3.76 (m, 4H), 3.85 (s, 3H), 4.00-4.20 (m, 2H), 4.32-4.51 (m, 1H), 6.77-7.21 (m, 1H), 7.48-7.82 (m, 3H), 7.87-7.92 (d, 1H, J=8.59 Hz), 8.12-8.22 (m, 2H), 8.33-8.35 (m, 3H), 8.68-8.75 (d, 1H, J=8.59 Hz); MS (FAB) 570 [M+H].$^+$ Example—6

(2S)—N-{4-[5-[1-(4-hydroxyphenyl)-3-(4-hydroxy-3-methoxyphenyl)-2-propen-1-one]pentyl]oxy]-5-methoxy-2-nitrobenzoyl}pyrrolidine-2-carboxaldehyde diethylthioacetal (4f)

The compound 4f has been prepared according to the method described for the compound 4a by employing the compounds (2S)—N-[4-(5-bromopentyloxy-5-methoxy-2-nitrobenzoyl]pyrrolidine-2-carboxaldehyde diethylthioacetal 2c (549 mg, 1.0 mmol) followed by anhydrous K$_2$CO$_3$ (690 mg, 3.0 mmol) and 4-hydroxy substituted chalcone 3b (270 mg, 1.0 mmol) to afford the compound 4f (665 mg, 90%).

$^1$H NMR (CDCl$_3$): delta 1.29-1.39 (m, 6H), 1.62-2.33 (m, 4H), 2.54 (s, 3H), 2.60 (s, 3H) 2.64-2.87 (m, 4H), 3.18-3.26 (m, 6H), 3.66-3.96 (m, 3H), 4.04-4.16 (m, 2H), 4.64-4.71 (m, 1H), 4.82-4.84 (d, 1H, J=3.79 HZ), 6.70-6.98 (m, 1H), 7.10-7.41 (m, 1H), 7.62-7.74 (m, 1H), 7.94-8.03 (d, 1H, J=7.68 Hz), MS (FAB) 738 [M+H]$^+$.

(2S)—N-{4-[4-[1-(4-fluorophenyl)-3-(4-hydroxy-3-methoxyphenyl)-2-propen-1-one]pentyl]oxy]-5-methoxy-2-aminobenzoyl}pyrrolidine-2-carboxaldehyde diethyl thioacetal (5f)

The compound 5f has been prepared according to the method described for the compound 5a by employing compound 4f (735 mg, 1.0 mmol) to afford compound 5f (550 mg, 80%), which, due to potential stability problems, was used directly in the next step 7-Methoxy-8-{3-[1-(4-hydroxyphenyl)-3-(4-hydroxy-3-methoxyphenyl)-2-propen-1-one]pentyl}-oxy-(11aS)-1,2,3,11a-5H-pyrrolo[2,1-][1,4]benzodiazepin-5-one (6f)

The compound 6f was prepared according to the method described for the compound 6a employing the compound 5f (705 mg, 1.0 mmol) to afford the compound 6f (445 mg, 72%).

$^1$H NMR (CDCl$_3$): delta 1.19-1.38. (m, 6H), 1.85-2.29 (m, 6H), 2.54 (s, 3H), 2.60 (s, 3H), 2.78 (m 4H), 2.97-3.19 (m, 4H), 3.24-3.77 (m, 4H), 3.89 (s, 3H), 4.03-4.20 (m, 2H), 4.33-4.52 (m, 1H), 6.76-7.24 (m, 1H), 7.49-7.84 (m, 3H), 7.87-7.95 (d, 1H, J=8.53 Hz), 8.16-8.22 (m, 2H), 8.34-8.40 (m, 3H), 8.68-8.79 (d, 1H, J=8.97 Hz); MS (FAB) 584 [M+H]$^+$ Example—7

(2S)—N-{4-[3-(4-hydroxy-3-methoxyphenyl)-1-(2,4-dimethyl-3-quinolyl)-2-propen-1-one]propyl]oxy]-5-methoxy-2-nitrobenzoyl}pyrrolidine-2-carboxaldehyde diethylthioacetal (8a)

To a solution of compound (2S)—N-[4-(5-bromopropyloxy-5-methoxy-2-nitrobenzoyl]pyrrolidine-2-carboxaldehyde diethylthioacetal 2a (521 mg, 1.0 mmol) in dry acetone (15 ml) was added, 3-(4-hydroxy-3-methoxyphenyl)-1-(2,4-dimethyl-3-quinolyl)-2-propen-1-one] 7a (319 mg, 1.0 mmol) followed by K$_2$CO$_3$ (690 mg, 3.0 mmol) and the reaction mixture was refluxed for 48 hrs. After the completion of the reaction as indicated by TLC, EtOAc:hexane (1:1), the reaction mixture was poured into the water and then extracted with ethyl acetate. This was concentrated under reduced pressure to obtain the crude product which was further purified by column chromatography on silica gel eluting with EtOAc: hexane (3:7) to give the pure compound 8a as yellow liquid (656 mg, 86%).

$^1$H NMR (CDCl$_3$): δ 1.22-1.39 (m, 4H), 1.67-2.32 (m, 4H), 2.58 (s, 3H), 2.60 (s, 3H) 2.62-2.68 (m, 3H), 2.71-2.88 (m, 4H), 3.18-3.28 (m, 2H), 3.86 (s, 3H), 3.95 (s, 3H), 4.02-4.21 (m, 4H), 4.65-4.74 (m, 1H), 4.85-4.89 (d, 1H, J=3.67 Hz), 6.80-7.14 (m, 7H), 7.55-7.80 (m, 3H), 7.96-8.06 (m 2H); MS (FAB) 775 [M+H]$^+$.

(2S)—N-{4-[3-(4-hydroxy-3-methoxyphenyl)-1-(2,4-dimethyl-3-quinolyl)-2-propen-1-one]propyl]oxy]-5-methoxy-2-aminobenzoyl}pyrrolidine-2-carboxaldehyde diethyl thioacetal (9a)

The compound 9a has been prepared according to the method described for the compound 4a by employing compound 8a (742 mg, 1.0 mmol) to afford compound 9a (664 mg, 95%), which, due to potential stability problems, was used directly in the next step.

7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one (10a)

A solution of 9a (730 mg, 1.0 mmol), HgCl$_2$ (678 mg, 2.26 mmol) and CaCO$_3$ (250 mg, 2.46 mmol) in acetonitrile-water (4:1) was stirred at room temperature for 12 h until the completion of the reaction as shown by TLC (EtOAc). The organic layer was evaporated in vacuum and the residue is diluted with EtOAc. To this a saturated aqueous solution of NaHCO$_3$ was added slowly at room temperature and the mixture was filtered through a celite bed and washed with ethyl acetate. The filtrate was evaporated in vacuum to get crude compound 10a, which was further purified by column chromatography on silica gel eluting first with ethyl acetate to remove traces of mercuric salts and then with CHCl$_3$:methanol (9:1) (441 mg, 75%).

$^1$H NMR (CDCl$_3$): δ 1.21-1.39 (m, 2H), 1.66-2.39 (m, 2H), 2.55 (s, 3H), 2.59 (s, 3H), (m, 4H), 2.94-3.02 (m, 2H), 3.15-3.26 (m, 2H), 3.85 (s, 3H), 3.91 (s, 3H), 4.20-4.32 (m, 2H), 6.76-7.08 (m, 7H), 7.51-7.57 (t, 1H, J=7.38 Hz), 7.67-7.74 (m, 2H), 7.95-8.06 (m, 2H); MS (FAB) 620 [M+H]$^+$.

Example—8

(2S)-N-{4-[4-[3-(4-hydroxy-3-methoxyphenyl)-1-(2,4-dimethyl-3-quinolyl)-2-propen-1-one]butyl]oxy]-5-methoxy-2-nitrobenzoyl}pyrrolidine-2-carboxaldehyde diethylthioacetal (8b)

The compound 8b has been prepared according to the method described for the compound 8a by employing the compounds (2S)-N-[4-(5-bromobutyloxy-5-methoxy-2-nitrobenzoyl]pyrrolidine-2-carboxaldehyde diethylthioacetal 2b (535 mg, 1.0 mmol) followed by K$_2$CO$_3$ (690 mg, 3.0 mmol) and 3-(4-hydroxy-3-methoxyphenyl)-1-(4-methyl-3-quinolyl)-2-propen-1-one 7b (319 mg, 1.0 mmol) to afford the compound 8b (686 mg, 88%).

$^1$H NMR (CDCl$_3$): delta 1.20-1.40 (m, 4H), 1.66-2.35 (m, 3H), 2.57, (s, 3H), 2.56 (s, 3H) 2.69 (s, 3H), 2.61-2.66 (m, 3H), 2.70-2:87 (m, 4H), 3.19-3.29 (m, 2H), 3.85 (s, 3H), 3.94 (s, 3H), 4.01-4.22 (m, 4H), 4.66-4.75 (m, 1H), 4.85-4.89 (d, 1H, J=3.67 Hz), 6.80-7.14 (m, 7H), 7.55-7.80 (m, 3H), 7.96-8.06 (m 2H); MS (FAB) 789 [M+1]$^+$.

(2S)-N-{4-[3-(4-hydroxy-3-methoxyphenyl)-1-(2,4-dimethyl-3-quinolyl)-2-propen-1-one]butyl]oxy]-5-methoxy-2-aminobenzoyl}pyrrolidine-2-carboxaldehyde diethylthioacetal (9b)

The compound 9b has been prepared according to the method described for the compound 4a by employing compound 8b (756 mg, 1.0 mmol) to afford compound 9b (588 mg, 91%), which due to potential stability problems, was used directly in the next step.

7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one (10b)

The compound 10b was prepared according to the method described for the compound 10a employing the compound 9b (745 mg, 1.0 mmol) to afford the compound 10b (440 mg, 70%).

$^1$H NMR (CDCl$_3$): δ 1.40-1.50 (d, 4H, J=6.1 Hz), 1.65-2.10 (m, 4H), 2.15 (s, 3H), 2.61-2.80 (m, 6H), 3.10-3.15 (m, 3H), 3.40-3.55 (m, 4H) 3.95 (s, 3H), 4.00-4.09 (m, 6H), 5.65 (s, 1H), 6.68-6.70 (d, 1H, J=9.2 Hz), 6.78 (s, 1H), 7.25-7.35 (d, 1H, J=8.3 Hz), 7.62 (s, 1H), 7.64-7.74 (d, 1H, J=3.7 Hz); MS (FAB) 634 [M+H]$^+$.

Example—9

(2S)-N-{4-[5-(4-hydroxy-3-methoxyphenyl)-1-(2,4-dimethyl-3-quinolyl)-2-propen-1-one]pentyl]oxy]-5-methoxy-2-nitrobenzoyl}pyrrolidine-2-carboxaldehyde diethylthioacetal (8c)

The compound 8c has been prepared according to the method described for the compound 8a by employing the compounds (2S)-N-[4-(5-bromopentyloxy-5-methoxy-2-nitrobenzoyl]pyrrolidine-2-carboxaldehyde diethylthioacetal 2c (549 mg, 1.0 mmol) followed by K$_2$CO$_3$ (690 mg, 3.0 mmol) and 3-[4-hydroxy-3-methoxyphenyl]-1-(2,4-dimethyl-3-quinolyl)-2-propen-1-one 7a (319 mg, 1.0 mmol) to afford the compound 8c (710 mg, 89%).

$^1$H NMR (CDCl$_3$): δ 1.20-1.41. (m, 6H), 1.65-2.34 (s, 6H), 2.57 (s, 3H), 2.60 (s, 3H) 2.62-2.67 m, 4H), 2.69-2.88 (m, 4H), 3.18-3.28 (m, 2H), 3.84 (s, 3H), 3.93 (s, 3H), 4.01-4.23 (m, 4H), 4.65-4.76 (m, 1H), 4.84-4.89 (d, 1H, J=3.67 Hz), 6.81-7.15 (m, 7H), 7.55-7.80 (m, 3H), 7.96-8.06 (m 2H); MS (FAB) 803 [M+H]$^+$ (2S)-N-{4-[5-[3-(4-hydroxy-3-methoxyphenyl)-1-(2,4-dimethyl-3-quinolyl)-2-propen-1-one]pentyl]oxy]-5-methoxy-2-aminobenzoyl}pyrrolidine-2-carboxaldehyde diethyl thioacetal (9c)

The compound 9c has been prepared according to the method described for the compound 4a by employing compound 8c (650 mg, 1.0 mmol) to afford compound 9c (614 mg, 83%), which, due to potential stability problems, was used directly in the next step.

7-Methoxy-8-{5-[3-(4-hydroxy-3-methoxyphenyl)-1-(2,4-dimethyl-3-quinolyl)-2-propen-1-one]pentyl}-oxy-(11aS)-1,2,3,11a-5H-pyrrolo[2,1-c][1,4]benzodiazepin-5-one (10c)

The compound 10c was prepared according to the method described for the compound 10a employing the compound 9c (730 mg, 1.0 mmol) to afford the compound 10c (465 mg, 73%).

$^1$H NMR (CDCl$_3$): δ 1.21-1.42 (m, 4H), 1.64-2.41 (m, 4H), 2.54-2.65 (m, 6H), 2.66-2.82 (m, 3H), 2.95-3.03 (2H), 3.14-3.25 (m, 2H), 3.87 (s, 3H), 3.93 (s, 3H), 4.20-4.34 (m, 2H), 6.75-7.08 (m, 7H), 7.51-7.59 (t, 1H, J=7.39 Hz), 7.65-7.75 (m, 2H), 7.93-8.07 (m, 2H); MS (FAB) 648 [M+H]$^+$.

Example—10

(2S)-N-{4-[3-(4-hydroxy-3-methoxyphenyl)-1-(2,4-dimethyl-3-quinolyl)-2-propen-1-one]hexyl]oxy]-5-methoxy-2-nitrobenzoyl}pyrrolidine-2-carboxaldehyde diethylthioacetal (8d)

The compound 8d has been prepared according to the method described for the compound 8a by employing the compounds (2S)-N-[4-(5-bromohexyloxy-5-methoxy-2-nitrobenzoyl]pyrrolidine-2-carboxaldehyde diethylthioacetal 2d (549 mg, 1.0 mmol) followed by K$_2$CO$_3$ (690 mg, 3.0 mmol) and 4-hydroxy-3-methoxyphenyl-1-(2,4-dimethyl-3-quinolyl)-2-propen-1-one 7a (319 mg, 1.0 mmol) to afford the compound 8d (725 mg, 90%).

$^1$H NMR (CDCl$_3$): δ 1.20-1.41 (m, 6H), 1.65-2.34 (m, 8H), 2.54 (s, 3H), 2.57 (s, 3H) 2.62-2.67 m, 4H), 2.69-2.88 (m, 3H), 3.18-3.28 (m, 2H), 3.84 (s, 3H), 3.93 (s, 3H), 4.01-4.23

(m, 4H), 4.65-4.76 (m, 1H), 4.84-4.89 (d, 1H, J=3.67 Hz), 6.81-7.15 (m, 7H), 7.55-7.80 (m, 3H), 7.96-8.06 (m 2H); MS (FAB) 817 [M+H]+

(2S)—N-{4-[5-[3-(4-hydroxy-3-methoxyphenyl)-1-(2,4-dimethyl-3-quinolyl)-2-propen-1-onehexyl]oxy]-5-methoxy-2-aminobenzoyl}pyrrolidine-2-carboxaldehyde diethylthioacetal (9d)

The compound 9d has been prepared according to the method described for the compound 4a by employing compound 8d (520 mg, 1.0 mmol) to afford compound 9d (634 mg, 86%), which, due to potential stability problems, was used directly in the next step.

7-Methoxy-8-{6-[3-(4-hydroxy-3-methoxyphenyl)-1-(2,4-dimethyl-3-quinolyl)-2-propen-1-one]hexyl}-oxy-(11aS)-1,2,3,11a-5H-pyrrolo[2,1-c][1,4]benzodiazepin-5-one (10d)

The compound 10d was, prepared according to the method described for the compound 10a employing the compound 9d (775 mg, 1.0 mmol) to afford the compound 10d (480 mg, 70%).

$^1$H NMR (CDCl$_3$): δ 1.21-1.44 (m, 6H), 1.65-2.42 (m, 4H), 2.54-2.64 (m, 6H), 2.66-2.82 (m, 3H), 2.95-3.04 (m, 2H), 3.15-3.27 (m, 2H), 3.87 (s, 3H), 3.94 (s, 3H), 4.20-4.34 (m, 2H), 6.75-7.09 (m, 7H), 7.50-7.59 (t, 1H, J=7.39 Hz), 7.65-7.76 (m, 2H), 7.93-8.06. (m, 2H); MS (FAB) 662 [M+H]+.

Biological Activity: The in vitro cell line studies were carried out at the National Cancer Institute, Maryland, USA.
Cytotoxicity:
The compounds 6b) 7-Methoxy-8-{4-[1-(4-fluorophenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one;
(6c) 7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one;
(6g) 7-Methoxy-8-{3-[1-(2-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one;
(10a) 7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one
(10b) 7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one;
were evaluated for in vitro anticancer activity against nine human tumour cells derived from nine cancer types (leukemia, ovarian, renal, melanoma, CNS, colon, prostate, lung, cervix and breast cancer) as shown in (Table 1, 2 and 3)

6b, 6c, 6g, 10a and 10b were evaluated for in vitro anticancer activity against sixty human tumour cells derived from nine cancer types (leukemia, non-small-cell lung, colon, CNS, melanoma, ovarian, prostate, renal and breast cancer) as shown in (Table 1 and 2). For the compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$ TGI and $\log_{10}$ LC50 as well as $\log_{10}$ GI50 for 6b, c, g and 10a-b listed in Table (1, 2 and 3). As demonstrated by mean graph pattern, compound 6a, b, g and 10a-b exhibited an interesting profile of activity and selectivity for various cell lines. The mean graph mid point of $\log_{10}$ TGI and $\log_{10}$ LC50 showed similar pattern to the $\log_{10}$ GI50 mean graph mid points.

TABLE 1

Log GI$_{50}$ (concentration in mol/L causing 50% growth inhibition) values for chalcone-PBD hybrids.

| Cancer Cell Lines | 6b | 6c | 6g | 10a | 10b |
|---|---|---|---|---|---|
| Leukemia | −6.84 | −6.59 | −5.62 | −6.88 | −6.94 |
| Non-small cell lung | −6.84 | −6.38 | −5.82 | −6.79 | −6.87 |
| Colon | −6.53 | −6.76 | −5.85 | −6.76 | −6.41 |
| CNS | −5.91 | −5.68 | −5.62 | −6.61 | −6.16 |
| Melanoma | −6.65 | −6.38 | −5.65 | −6.38 | −6.59 |
| Ovarian | −5.56 | −4.60 | −5.56 | −5.10 | −5.28 |
| Renal | −6.67 | −6.39 | −5.67 | −6.39 | −6.17 |
| Prostate | −5.63 | −5.05 | −4.63 | −5.05 | −5.85 |
| Breast | −6.57 | −6.31 | −6.57 | −6.31 | −6.52 |

Each cancer type represents the average of six to eight different cancer cell lines.

TABLE 2

Log$_{10}$ GI50 log$_{10}$TGI and log$_{10}$LC50 mean graphs midpoints (MG_MID) of in vitro cytotoxicity data for the representative compounds against human tumour cell lines

| Compound | Log$_{10}$GI50 | Log$_{10}$TGI | Log$_{10}$LC50 |
|---|---|---|---|
| 6b | −6.83 | −6.81 | −4.59 |
| 6c | −6.86 | −6.79 | −4.61 |
| 6g | −5.78 | −5.86 | −4.58 |
| 10a | −6.94 | −6.90 | −4.43 |
| 10b | −6.86 | −6.94 | −4.46 |

TABLE 3

Cytotoxicity of compounds 6b, c, g and 10a, b in selected cancer cell lines

| Cancer panel/ cell line | GI$_{50}$ (μM) 6b | GI$_{50}$ (μM) 6c | GI$_{50}$ (μM) 6g | GI$_{50}$ (μM) 10a | GI$_{50}$ (μM) 10b |
|---|---|---|---|---|---|
| Leukemia | | | | | |
| CCRF-CEM | 16.0 | 25.1 | 37.4 | 12.5 | 13.4 |
| HL-60(TB) | 29.0 | 28.2 | 49.5 | 25.2 | 24.5 |
| RPMI-8226 | 13.0 | 16.4 | 46.8 | 15.0 | 13.8 |
| Non-small cell lung | | | | | |
| NCI-H226 | 14.0 | 16.5 | 28.4 | 10.8 | 10.1 |
| NCI-H23 | 19.2 | 15.8 | 22.5 | 24.1 | 19.5 |
| NCI-H522 | 11.5 | 65.3 | 18.3 | 10.8 | 9.0 |
| Colon | | | | | |
| HCT-116 | 11.2 | 21.0 | 14.6 | 21.0 | 14.6 |
| HCT-15 | 28.5 | 29.3 | 18.4 | 29.7 | 18.4 |
| SW-620 | 13.5 | 18.8 | 26.9 | 26.6 | 25.9 |
| CNS | | | | | |
| SF-539 | 29.6 | 30.3 | 33.7 | 30.3 | 33.7 |
| U251 | 14.8 | 15.2 | 19.8 | 19.8 | 15.7 |

TABLE 3-continued

Cytotoxicity of compounds 6b, c, g and
10a, b in selected cancer cell lines

| Cancer panel/ cell line | $GI_{50}$ (μM) 6b | $GI_{50}$ (μM) 6c | $GI_{50}$ (μM) 6g | $GI_{50}$ (μM) 10a | $GI_{50}$ (μM) 10b |
|---|---|---|---|---|---|
| Melanoma | | | | | |
| LOX IMVI | 10.0 | 18.2 | 15.0 | 18.2 | 15.0 |
| MALME-3M | 18.2 | 24.2 | 36.2 | 24.2 | 36.2 |
| M14 | 10.1 | 14.5 | 18.8 | 14.5 | 18.8 |
| SK-MEL-5 | 10.0 | 20.9 | 23.3 | 20.9 | 23.3 |
| UACC-257 | 70.9 | 22.9 | 15.9 | 22.9 | 15.9 |
| UACC-62 | 10.0 | 15.1 | 22.5 | 15.1 | 22.5 |
| Ovarian | | | | | |
| OVCAR-3 | 37.0 | 34.3 | 46.3 | 24.9 | 26.3 |
| Renal | | | | | |
| 786-0 | 19.8 | 18.4 | 24.9 | 17.3 | 14.9 |
| A498 | 26.1 | 20.1 | 29.0 | 20.1 | 19.5 |
| ACHN | 43.4 | 42.0 | 46.1 | 32.0 | 36.1 |
| CAKI-1 | 13.6 | 15.8 | 22.9 | 15.8 | 12.9 |
| TK-10 | 16.6 | 38.2 | 31.4 | 33.2 | 31.4 |
| UO-31 | 19.2 | 21.1 | 45.2 | 21.6 | 15.2 |
| Breast | | | | | |
| NCI/ADR-RES | 13.8 | 17.4 | 28.7 | 17.6 | 16.9 |
| MDA-MB-231/ATCC | 11.6 | 19.9 | 14.2 | 19.9 | 14.2 |

Each cancer type represents the average of six to nine different cancer cell lines. In vitro evaluation of cytotoxic activity. The compound 6b, 6c, 6g 10a and 10b were evaluated for in vitro anticancer activity against nine human tumour cells derived from six cancer types (leukemia, colon, prostate, melanoma, ovarian, lung, cervix and breast cancer) as shown in Table 3. Compounds 6b, 6c, 10a and 10b show promising cytotoxicity against some cancer cell lines (Table 3). Compounds 6b, 6c, 6g, 10a and 10b have been evaluated for their in vitro cytotoxicity in selected human cancer cell lines of colon (Colo205), lung (NCI-H522, NCI-H226), colon (colo-205), prostate (DU145, PC3), ovarian (IGROV1, HT1080), and breast (MDA-MB-435, Zr-75-1), melanoma (LOXMIVI, VACC-62, SK-MEL-5) origin. A protocol of 48 h continuous drug exposure has been used and an Adriamycin (ADR) protein assay has been used to estimate cell viability or growth. The results are expressed as percent of cell growth determined relative to that of untreated control cells Thermal Denaturation Studies These compounds have also been subjected to thermal denaturation studies with duplex-form calf thymus DNA (CT-DNA) using an modification of a reported procedure. Working solutions in aqueous buffer (10 mM $NaH_2PO_4$/$Na_2HPO_4$, 1 mM $Na_2EDTA$, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. $min^{-1}$ in the 40-110° C. range. DNA helix→coil transition temperatures ($T_m$) have been obtained from the maxima in the $d(A_{260})/dT$ derivative plots. Drug-induced alterations in DNA melting behavior are given by: $\Delta T_m = T_m(DNA+PBD) - T_m(DNA\ alone)$, where the $T_m$ value for the PBD-free CT-DNA is 68.5±0.01. The fixed [PBD]/[DNA] ratio used has not resulted in binding saturation of the host DNA duplex for any compound examined.

The DNA binding activity for these novel C8-linked chalcone-PBD hybrids has been examined by thermal denaturation studies using calf thymus (CT) DNA.[25] Melting studies show that these compounds stabilize the thermal helix→coil or melting stabilization ($\Delta T_m$) for the CT-DNA duplex at pH 7.0, incubated at 37° C., where PBD/DNA molar ratio is 1:5. Interestingly, in this assay one of the chalcone-PBD hybrids (6a-d) elevates the helix melting temperature of CT-DNA by a margin of 17.5° C. after incubation for 18 h at 37° C. Data for 6a-d, 10a-d and DC-81 are included in Table 4.

TABLE 4

Thermal denaturation data for chalcones-
PBD hybrids with calf thymus (CT) DNA

| PBD hybrids | [PBD]:[DNA] molar ratio[b] | $\Delta T_u$ (° C.)[a] after incubation at 37 □C. for 0 h | 18 h |
|---|---|---|---|
| 6a | 1:5 | 1.7 | 2.4 |
| 6b | 1:5 | 2.2 | 2.6 |
| 5c | 1:5 | 2.4 | 2.9 |
| 6d | 1:5 | 2.1 | 2.6 |
| 10a | 1:5 | 4.0 | 4.6 |
| 10b | 1:5 | 4.3 | 4.9 |
| 10c | 1:5 | 4.7 | 5.1 |
| 10d | 1:5 | 4.9 | 5.3 |
| DC-81 | 1:5 | 0.3 | 0.7 |

[a]For CT-DNA alone at pH 7.00 ± 0.01, $T_m$ = 68.5° C. ± 0.01 (mean value from 10 separate determinations), all $\Delta T_m$ values are ±0.1-0.2° C.
[b]For a 1:5 molar ratio of [PBD]/[DNA], where CT-DNA concentration = 100 μM and ligand concentration = 20 μM in aqueous sodium phosphate buffer[10 mM sodium phosphate + 1 mM EDTA, p
[a]For CT-DNA alone at pH 7.00 ± 0.01, $T_m$ = 69.6° C. ± 0.01 (mean value from 10 separate determinations), all $\Delta T_m$ values are ±0.1-0.2° C.
[b]For a 1:5 molar ratio of [ligand]/[DNA], where CT-DNA concentration = 100 μM and ligand concentration = 20 μM in aqueous sodium phosphate buffer [10 mM sodium phosphate + 1 mM EDTA, pH 7.00 ± 0.01].

ADVANTAGES OF THE INVENTION

1. The present invention provides a new pyrrolo[2,1-c][1,4]benzodiazepine hybrids useful as antitumour agents.

2. It also provides a process for the preparation of novel pyrrolo[2,1-c][1,4]benzodiazepine hybrids

We claim:

1. A compound of formula 6 and or formula 10

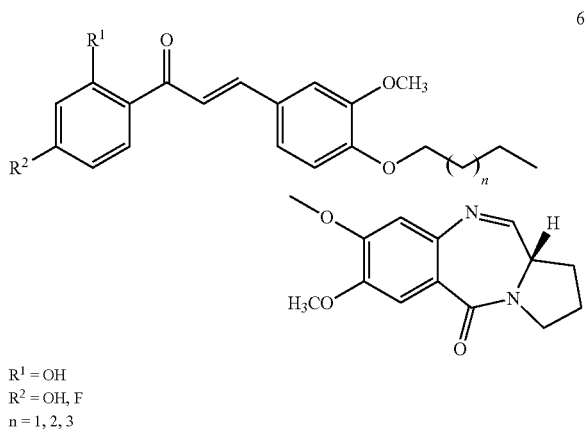

6

$R^1$ = OH
$R^2$ = OH, F
n = 1, 2, 3

-continued

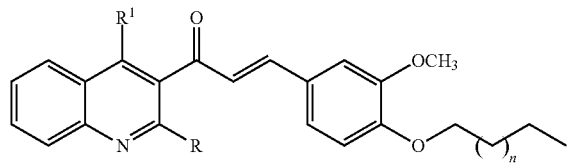

R¹ = methyl, ethyl, phenyl
R = methyl
n = 1, 2, 3, 4

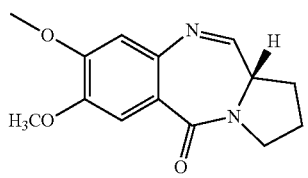

wherein R¹=OH, methyl, ethyl or phenyl; R²=H, OH or F: R=H or methyl; and n=1-4.

2. The compound as claimed in claim 1, wherein said compound is selected from the group consisting of 7-Methoxy-8-{3-[1-(4-fluorophenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6a);

7-Methoxy-8-{4-[1-(4-fluorophenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6b);

7-Methoxy-8-{5-[1-(4-fluorophenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6c);

7-Methoxy-8-{3-[1-(2-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6d);

7-Methoxy-8-{4-[1-(2-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6e);

7-Methoxy-8-{5-[1-(2-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6f);

7-Methoxy-8-{3-[1-(4-hydroxyphenyl)-3-(4-hydroxy-3-methoxyphenyl)-2-propen-1-one]propyl}-oxy-(11aS)-1,2,3,11a-5H-pyrrolo[2,1-c][1,4]benzodiazepin-5-one (6 g);

7-Methoxy-8-{4-[1-(4-hydroxyphenyl)-3-(4-hydroxy-3-methoxyphenyl)-2-propen-1-one]butyl}-oxy-(11aS)-1,2,3,11a-5H-pyrrolo[2,1-c][1,4]benzodiazepin-5-one (6h);

7-Methoxy-8-{5-[1-(4-hydroxyphenyl)-3-(4-hydroxy-3-methoxyphenyl)-2-propen-1-one]pentyl}-oxy-(11aS)-1,2,3,11a-5H-pyrrolo[2,1-c][1,4]benzodiazepin-5-one (6i);

7-Methoxy-8-{3-[3-(4-hydroxy-3-methoxyphenyl)-1-(2,4-dimethyl-3-quinolyl)-2-propen-1-one]propyl}-oxy-(11aS)-1,2,3,11a-5H-pyrrolo[2,1-c][1,4]benzodiazepin-5-one (10a);

7-Methoxy-8-{4-[3-(4-hydroxy-3-methoxyphenyl)-1-(2,4-dimethyl-3-quinolyl)-2-propen-1-one]butyl}-oxy-(11aS)-1,2,3,11a-5H-pyrrolo[2,1-c][1,4]benzodiazepin-5-one (10b);

7-Methoxy-8-{5-[3-(4-hydroxy-3-methoxyphenyl)-1-(2,4-dimethyl-3-quinolyl)-2-propen-1-one]pentyl}-oxy-(11aS)-1,2,3,11a-5H-pyrrolo[2,1-c][1,4]benzodiazepin-5-one (10c);

7-Methoxy-8-{6-[3-(4-hydroxy-3-methoxyphenyl)-1-(2,4-dimethyl-3-quinolyl)-2-propen-1-one]hexyl}-oxy-(11aS)-1,2,3,11a-5H-pyrrolo[2,1-c][1,4]benzodiazepin-5-one (10d);

7-Methoxy-8-{3-[3-(4-hydroxy-3-methoxyphenyl)-1-(2-methyl-4-phenyl-3-quinolyl)-2-propen-1-one]propyl}-oxy-(11aS)-1,2,3,11a-5H-pyrrolo[2,1-c][1,4]benzodiazepin-5-one (10e);

7-Methoxy-8-{4-[3-(4-hydroxy-3-methoxyphenyl)-1-(2-methyl-4-phenyl-3-quinolyl)-2-propen-1-one]butyl}-oxy-(11aS)-1,2,3,11a-5H-pyrrolo[2,1-c][1,4]benzodiazepin-5-one (10f);

7-Methoxy-8-{5-[3-(4-hydroxy-3-methoxyphenyl)-1-(2-methyl-4-phenyl-3-quinolyl)-2-propen-1-one]pentyl}-oxy-(1aS)-1,2,3,11a-5H-pyrrolo[2,1-c][1,4]benzodiazepin-5-one (10g);

7-Methoxy-8-{6-[3-(4-hydroxy-3-methoxyphenyl)-1-(2-methyl-4-phenyl-3-quinolyl)-2-propen-1-one]hexyl}-oxy-(11aS)-1,2,3,11a-5H-pyrrolo[2,1-c][1,4]benzodiazepin-5-one (10h);

7-Methoxy-8-{3-(4-hydroxy-3-methoxyphenyl)-1-(2-methyl-4-ethyl-3-quinolyl)-2-propen-1-one]propyl}-oxy-(11aS)-1,2,3,11a-5H-pyrrolo[2,1-c][1,4]benzodiazepin-5-one (10i);

7-Methoxy-8-{4-[3-(4-hydroxy-3-methoxyphenyl)-1-(2-methyl-4-ethyl-3-quinolyl)-2-propen-1-one]butyl}-oxy-(11aS)-1,2,3,11a-5H-pyrrolo[2,1-c][1,4]benzodiazepin-5-one (10j);

7-Methoxy-8-{5-[3-(4-hydroxy-3-methoxyphenyl)-1-(2-methyl-4-ethyl-3-quinolyl)-2-propen-1-one]pentyl}-oxy-(11aS)-1,2,3,11a-5H-pyrrolo[2,1-c][1,4]benzodiazepin-5-one (10k); and 7-Methoxy-8-{6-[3-(4-hydroxy-3-methoxyphenyl)-1-(2-methyl-4-ethyl-3-quinolyl)-2-propen-1-one]hexyl}-oxy-(11aS)-1,2,3,11a-5H-pyrrolo[2,1-c][1,4]benzodiazepin-5-one (10l).

3. A pharmaceutical composition comprising a compound of claim 1 and a pharmaceutically acceptable carrier, optionally further comprising adjuvants and additives.

4. The pharmaceutical composition as claimed in claim 3, wherein the compound is represented by a general formula 6a-i and 10a-l

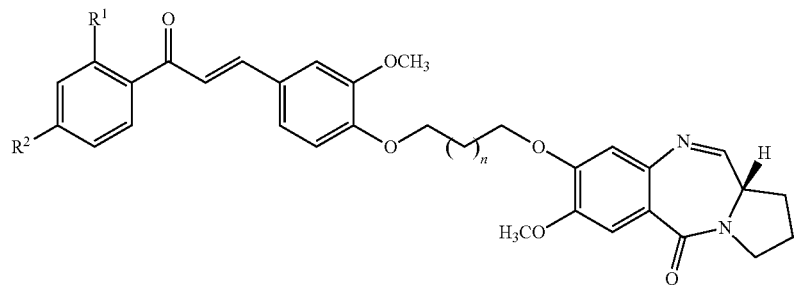
6a-i
R[1] = OH
R[2] = OH, F
n = 1, 2, 3
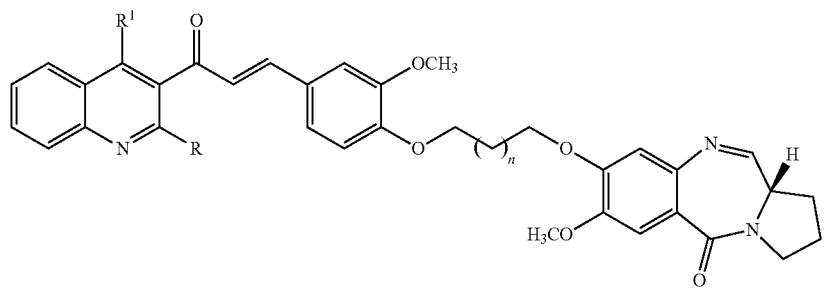
10a-I
R[1] = methyl, ethyl, phenyl
R = methyl
n = 1, 2, 3, 4
5. A process for the preparation of a compound of formula 6 or 10
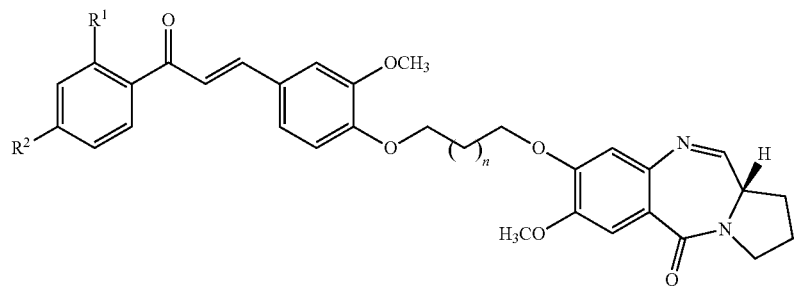
6
R[1] = OH
R[2] = OH, F
n = 1, 2, 3
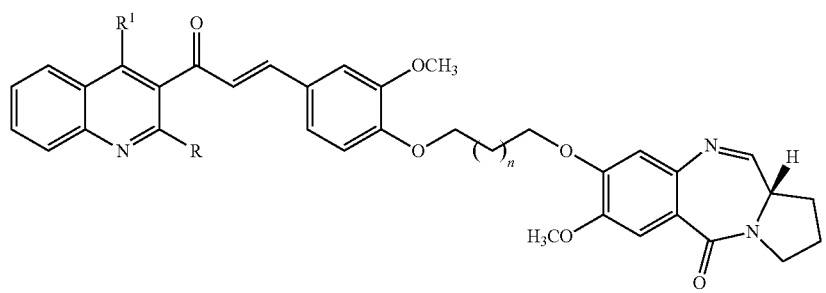
10
R = methyl
R = methyl, ethyl, phenyl
n = 1, 2, 3, 4 wherein n=1-4, comprising the steps of:

a) reacting (2S)—N-[4-(n-bromoalkyl)oxy-5-methoxy-2-nitrobenzoyl]pyrrolidine-2-carboxaldehyde diethylthioacetal of formula 2

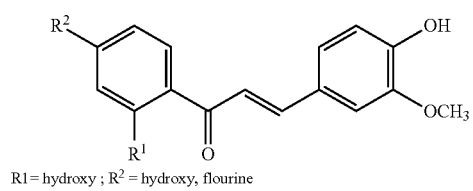

with a chalcone derivative selected from the compounds of formula 3 and 7

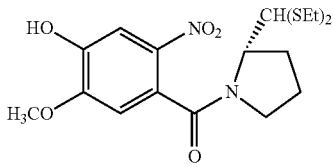

Formula 3

R1 = hydroxy ; R² = hydroxy, flourine

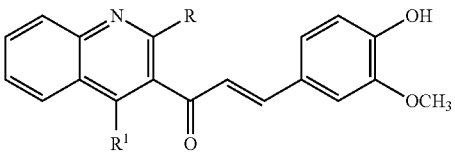

Formula 7

R = methyl
R¹ = methyl, ethyl, phenyl in the presence of an inorganic base, said base is selected from a group of $K_2CO_3$ and $CH_3COCH_3$, in an aprotic organic solvent, under refluxing temperature to obtain the resultant nitro compounds of (2S)—N-{n-[1-(alkyl phenyl)-3-(4-hydroxy-3-methoxyphenyl)-2-propen-1-one]-5-methoxy-2-nitro benzoyl}-pyrrolidine-2-carboxaldehyde diethylthioacetal of formula 4a-i, or (2S)—N-[n-(4-hydroxy-3-methoxyphenyl)-1-(2-methyl-4-methyl-3-quinolyl)-2-propen-1-one]-5-methoxy-2-nitrobenzoyl}-pyrrolidine-2-carboxaldehyde diethylthioacetal of formula 8a-l

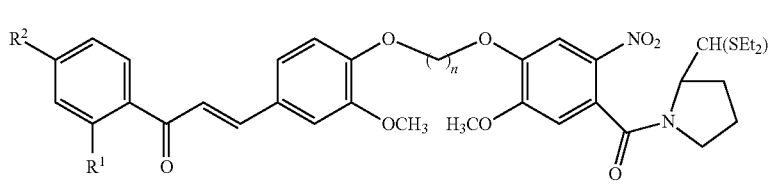

4a-i

R¹ = OH; R² = OH, F

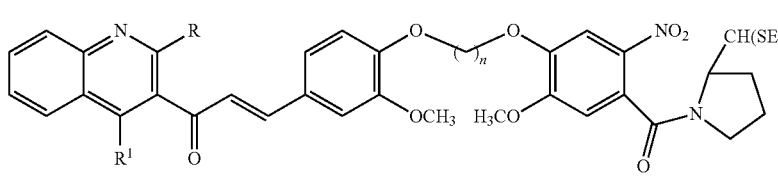

8a-l

R = methyl
R¹ = methyl, ethyl, phenyl b) reducing the above said nitro compounds of formula 4 or 8 obtained in step (a) with $SnCl_2.2H_2O$ in an organic solvent, under reflux temperature and isolating the corresponding amino compounds of (2S)—N-{4-[n-[1-(2 or 4-substituted phenyl)-3-(4-hydroxy-3-methoxyphenyl)-2-propen-1-one]alkyl]oxy]-5-methoxy-2-aminobenzoyl}pyrrolidine-2-carboxaldehyde diethyl thioacetal of formula 5a-i, or (2S)—N-{n-(4-hydroxy-3-methoxyphenyl)-1-(4-methyl-3-quinolyl)-2-propen-1-one]-5-methoxy-2-aminobenzoyl}-pyrrolidine-2-carboxaldehyde diethyl thioacetal of formula 9a-l

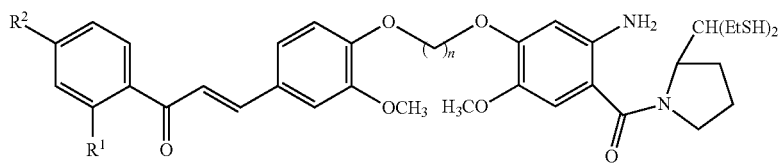

$R^1$ = OH; $R^2$ = OH, F

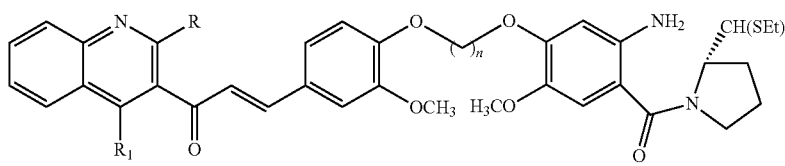

R = methyl
$R^1$ = methyl, ethyl, phenyl c) reacting the above said amino compounds of formula 5 or 9 obtained in step (b) with a deprotecting agent in the presence of an organic solvent to obtain the desired product of formula 6a-1 or 10a-1.

6. The process as claimed in claim 5, wherein the inorganic base used in step (a) is potassium carbonate.

7. The process as claimed in claim 5, wherein the aprotic organic solvent used in step (a) is acetone and acetonitrile.

8. The process as claimed in claim 5, wherein the organic solvent used in step (c) is acetonitrile.

9. The process as claimed in claim 5, wherein the organic solvent used in step (b) is an alcohol selected from a group of methanol and ethanol.

10. A method for treating cancer in a human comprising administering a therapeutically effective amount of a compound according to claim 1 to said human wherein the cancer is selected from the group consisting of lung, breast, colon and prostate cancer.

* * * * *